US010222392B2

(12) United States Patent
Wang et al.

(10) Patent No.: US 10,222,392 B2
(45) Date of Patent: Mar. 5, 2019

(54) SYSTEM AND METHOD FOR SCREENING A LIBRARY OF SAMPLES

(71) Applicants: The Johns Hopkins University, Baltimore, MD (US); Pioneer Hi-Bred International, Inc., Johnston, IA (US)

(72) Inventors: Tza-huei J. Wang, Timonium, MD (US); Tushar Dnyandeo Rane, Baltimore, MD (US); Helena Claire Zec, Baltimore, MD (US); Wen-Chy Chu, Baltimore, MD (US)

(73) Assignees: The Johns Hopkins University, Baltimore, MD (US); Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 15/146,319

(22) Filed: May 4, 2016

(65) Prior Publication Data

US 2016/0245837 A1  Aug. 25, 2016
US 2017/0261527 A9  Sep. 14, 2017

Related U.S. Application Data

(62) Division of application No. 13/708,510, filed on Dec. 7, 2012.

(Continued)

(51) Int. Cl.
*C40B 60/14* (2006.01)
*G01N 35/08* (2006.01)
(Continued)

(52) U.S. Cl.
CPC .......... *G01N 35/08* (2013.01); *B01J 19/0046* (2013.01); *B01L 3/0241* (2013.01);
(Continued)

(58) Field of Classification Search
CPC ................. B01L 3/502769; B01L 7/52; B01L 2200/0673; B01L 2200/10;
(Continued)

(56) References Cited

U.S. PATENT DOCUMENTS 6,762,018 B1  7/2004  Merenkova
7,749,737 B2  7/2010  McBride et al.
(Continued)

FOREIGN PATENT DOCUMENTS

EP           2481815 A1    8/2012
WO    WO-2003/036298 A2    5/2003
(Continued)

OTHER PUBLICATIONS

Abate et al., Proc. Natl. Acad. Sci. U. S. A., Nov. 2010, 107, 19163-19166 (DOI:10.1073/pnas.1006888107).
(Continued)

*Primary Examiner* — Dean Kwak
(74) *Attorney, Agent, or Firm* — Venable LLP; Henry J. Daley

(57) ABSTRACT

A continuous throughput microfluidic system includes an input system configured to provide a sequential stream of sample plugs; a droplet generator arranged in fluid connection with the input system to receive the sequential stream of sample plugs and configured to provide an output stream of droplets; a droplet treatment system arranged in fluid connection with the droplet generator to receive the output stream of droplets in a sequential order and configured to provide a stream of treated droplets in the sequential order; a detection system arranged to obtain detection signals from the treated droplets in the sequential order; a control system configured to communicate with the input system, the droplet generator, and the droplet treatment system; and a data
(Continued)

processing and storage system configured to communicate with the control system and the detection system.

9 Claims, 11 Drawing Sheets

Related U.S. Application Data

(60) Provisional application No. 61/638,245, filed on Apr. 25, 2012, provisional application No. 61/638,241, filed on Apr. 25, 2012, provisional application No. 61/567,837, filed on Dec. 7, 2011.

(51) Int. Cl.
*G01N 1/28* (2006.01)
*B01J 19/00* (2006.01)
*B01L 3/02* (2006.01)
*B01L 3/00* (2006.01)
*G01N 35/00* (2006.01)
*C40B 60/12* (2006.01)

(52) U.S. Cl.
CPC ....... *B01L 3/0265* (2013.01); *B01L 3/502715* (2013.01); *B01L 3/502784* (2013.01); *G01N 1/28* (2013.01); *G01N 35/00029* (2013.01); *G01N 35/00871* (2013.01); *B01L 2200/027* (2013.01); *B01L 2200/0673* (2013.01); *B01L 2200/14* (2013.01); *B01L 2200/143* (2013.01); *B01L 2200/147* (2013.01); *B01L 2300/0829* (2013.01); *B01L 2300/0838* (2013.01); *B01L 2300/0883* (2013.01); *B01L 2300/18* (2013.01); *B01L 2300/1822* (2013.01); *C40B 60/12* (2013.01); *G01N 2035/00148* (2013.01)

(58) Field of Classification Search
CPC ....... B01L 2300/088; B01L 2400/0481; B01L 3/502715; B01L 3/502753; B01L 2200/027; B01L 2200/147; B01L 2300/0838; B01L 2300/0864; B01L 2300/0883; B01L 2300/1822; B01L 2400/0406; B01L 3/0265; B01L 3/502723; B01L 3/50851; C12Q 1/686; C12Q 2563/116; C12Q 2563/143; C12Q 2563/159; C12Q 1/6825; C12Q 2523/125; C12Q 2531/113; C12Q 2547/107; C12Q 1/6806
USPC ................ 422/73, 82.01, 501–504; 436/180
See application file for complete search history.

(56) References Cited

U.S. PATENT DOCUMENTS

| | | | | |
|---|---|---|---|---|
| 7,815,871 | B2* | 10/2010 | Pamula | B41J 2/17509 204/643 |
| 8,133,703 | B2 | 3/2012 | Ching et al. | |
| 8,137,917 | B2 | 3/2012 | Pollack et al. | |
| 8,871,444 | B2* | 10/2014 | Griffiths | B01F 3/0807 435/6.1 |
| 9,328,344 | B2* | 5/2016 | Link | B01F 13/0071 |
| 2005/0202489 | A1* | 9/2005 | Cho | B01L 3/5027 435/6.12 |
| 2005/0262489 | A1 | 11/2005 | Streeter et al. | |
| 2006/0282224 | A1 | 12/2006 | Lee et al. | |
| 2006/1028222 | | 12/2006 | Lee et al. | |
| 2007/0003442 | A1* | 1/2007 | Link | G01N 15/1459 422/400 |
| 2007/0039866 | A1* | 2/2007 | Schroeder | B01L 3/502715 210/265 |
| 2007/0114180 | A1 | 5/2007 | Ramanathan et al. | |
| 2009/0325276 | A1 | 12/2009 | Battrell et al. | |
| 2010/0137163 | A1* | 6/2010 | Link | B01F 13/0071 506/16 |
| 2010/0173394 | A1* | 7/2010 | Colston, Jr. | B01L 3/502715 435/287.2 |
| 2010/0216244 | A1 | 8/2010 | Wu et al. | |
| 2011/0244455 | A1 | 10/2011 | Larson et al. | |
| 2011/0311978 | A1* | 12/2011 | Makarewicz, Jr. | B01F 3/0807 435/6.12 |
| 2012/0034602 | A1 | 2/2012 | Emig et al. | |
| 2012/0190032 | A1 | 7/2012 | Ness et al. | |
| 2012/0219947 | A1 | 8/2012 | Yurkovetsky et al. | |
| 2015/0238965 | A1* | 8/2015 | Beer | B01F 3/0807 422/505 |

FOREIGN PATENT DOCUMENTS

| | | |
|---|---|---|
| WO | WO-2007/133710 A2 | 11/2007 |
| WO | WO-2008/115626 A2 | 9/2008 |
| WO | WO-2008/147568 A1 | 12/2008 |
| WO | WO-2009/011808 A1 | 1/2009 |
| WO | WO-2010/025988 A1 | 3/2010 |
| WO | WO-2011/073643 A1 | 6/2011 |
| WO | WO-2012/038462 A1 | 3/2012 |

OTHER PUBLICATIONS

Abramoff et al., "Image Processing with Image," J Biophotonics International 2004, 11, 36-42.

Adamson et al., "Production of arrays of chemically distinct nanolitre plugs via repeated splitting in microfluidic devices," Lab. Chip 2006, 6, 1178-1186.

Baret et al., Lab. Chip, 2009, 9, 1850-1858 (DOI:10.1039/b902504a).

Beer et al., Anal. Chem., 2007, 79, 8471-8475 (DOI:10.1021/ac701809w).

Boedicker et al., Lab. Chip, 2008, 8, 1265-1272 (DOI:10.1039/b804911d).

Brouzes et al., "Droplet microfluidic technology for single-cell high-throughput screening," Proc. Natl. Acad. Sci. U. S. A. 2009, 106, 14195-14200.

Chen et al., "Microfluidic cartridges preloaded with nanoliter plugs of reagents: an alternative to 96-well plates for screening," Curr. Opin. Chem. Biol. 2006, 10, 226-231.

Clausell-Tormos et al., Chem. Biol., 2008, 15, 427-437 (DOI:10.1016/j.chembiol.2008.04.004).

Guo et al., Appl. Phys. Lett., 2010, 97, 233701-3.

Guo et al., Lab. Chip, Jan. 2012, (DOI:10.1039/c2lc21147e).

Gupta et al., *Heredity (Edinb)*, 2008, 101, 5-18 (DOI:10.1038/hdy.2008.35).

Huebner et al., Chem. Commun. (Camb), 2007, (12), 1218-1220 (DOI:10.1039/b618570c).

Huebner et al., Lab. Chip, 2008, 8, 1244-1254 (DOI:10.1039/b806405a).

Kiss et al., "High-throughput quantitative polymerase chain reaction in picoliter droplets," Anal. Chem. 2008, 80, 8975-8981.

Kumaresan et al., Anal. Chem., 2008, 80, 3522-3529 (DOI:10.1021/ac800327d).

Li et al., "Nanoliter microfluidic hybrid method for simultaneous screening and optimization validated with crystallization of membrane proteins," Proc. Natl. Acad. Sci. U. S. A. 2006, 103, 19243-19248.

Linder et al., "Reagent-loaded cartridges for valveless and automated fluid delivery in microfluidic devices," Anal. Chem. 2005, 77, 64-71.

Mayr et al., "Novel trends in high-throughput screening," Curr. Opin. Pharmacol. 2009, 9, 580-588.

Melin et al., Annu. Rev. Biophys. Biomol. Struct., 2007, 36, 213-231 (DOI:10.1146/annurev.biophys.36.040306.132646).

Pompano et al., Annu. Rev. Anal. Chem. (Palo Alto Calif), Mar. 2011, 4, 59-81 (DOI:10.1146/annurev.anchem.012809.102303).

Puleo et al., Lab. Chip, 2008, 8, 822-825 (DOI:10.1039/b717941c).

(56) References Cited

OTHER PUBLICATIONS

Puleo et al., Lab. Chip, 2009, 9, 1065-1072 (DOI:10.1039/b819605b).

Ragoussis, Annu. Rev. Genomics Hum. Genet., 2009, 10, 117-133 (DOI:10.1146/annurev-genom-082908-150116).

Rane et al., "Counting single molecules in sub-nanolitre droplets," Lab. Chip 2010, 10, 161-164.

Shi et al., Lab. Chip, 2008, 8, 1432-1435 (DOI:10.1039/b808753a).

Shi et al., Lab. Chip, Jan. 2010, 10, 2855-2863 (DOI:10.1039/c01c00256a).

Sobrino et al., Forensic Sci. Int., 2005, 154, 181-194 (DOI:10.1016/j.forsciint.2004.10.020).

Song et al., Angew. Chem. Int. Ed Engl., 2006, 45, 7336-7356 (DOI:10.1002/anie.200601554).

Teh et al., "Droplet microfluidics," Lab. Chip 2008, 8, 198-220.

Tewhey et al., *Nat. Biotechnol.*, 2009, 27, 1025-1031 (DOI:10.1038/nbt.1583).

Theberge et al., Lab. Chip, Jan. 2012, 12, 1320-1326 (DOI:10.1039/c2lc21019c).

Unger et al., *Science*, 2000, 288, 113-116.

Veldhuisen et al., *Vox Sang.*, 2009, 97, 198-206 (DOI:10.1111/j.1423-0410.2009.01209.x).

Wang et al., *ACS Nano*, 2010, 4, 6235-6243 (DOI:10.1021/nn101908e).

Zeng et al., *Lab. Chip*, 2009, 9, 1340-1343 (DOI:10.1039/b821803j).

Zhang et al., "Microfluidic DNA amplification—a review," *Anal. Chim. Acta* 2009, 638, 115-125.

Zheng et al., "A microfluidic approach for screening submicroliter volumes against multiple reagents by using preformed arrays of nanoliter plugs in a three-phase liquid/liquid/gas flow," *Angew. Chem. Int. Ed Engl.* 2005, 44, 2520-2523.

Zhong et al., "Multiplex digital PCR: breaking the one target per color barrier of quantitative PCR," Lab. Chip Apr. 2011, 11, 2167-2174.

\* cited by examiner a b c

SYSTEM AND METHOD FOR SCREENING A LIBRARY OF SAMPLES

This application is a divisional of U.S. patent application Ser. No. 13/708,510 filed on Dec. 7, 2012, which claims priority to U.S. Provisional Application Nos. 61/567,837 filed Dec. 7, 2011; 61/638,241 filed Apr. 25, 2012; and 61/638,245 filed Apr. 25, 2012; the entire contents of all of which are hereby incorporated by reference.

CROSS-REFERENCE OF RELATED APPLICATION

This application claims priority to U.S. Provisional Application Nos. 61/567,837 filed Dec. 7, 2011; 61/638,241 filed Apr. 25, 2012; 61/638,245 filed Apr. 25, 2012; the entire contents of all of which are hereby incorporated by reference.

BACKGROUND

1. Field of Invention

The field of the currently claimed embodiments of this invention relates to microfluidic systems, and more particularly to continuous throughput microfluidic systems.

2. Discussion of Related Art

High throughput sample processing is a critical requirement for a large number of industries. Some examples include the agricultural, pharmaceutical and biotechnological industries[1]. As a result, there is a constant drive for innovation in sample processing techniques to support these industries. One major breakthrough in this domain has been the application of various robotic sample handling techniques, to improve the speed of sample processing as well as to reduce the volume of reagents used per reaction. Although the robotic systems have become incredibly fast at sample processing operations, they are typically limited to operating with standard multi-well (96, 384 and 1536 well) plates. As a result, the typical sample volume consumption is on the order of microliters per reaction for such systems[1]. Recent advances in the microfluidic domain show promise in overcoming this limitation of the robotic systems. Droplet-based microfluidic systems have been shown to be capable of performing biomolecular screening with sample volumes as low as picoliters[2-6]. However, introducing a large number of samples on a miniature microfluidic device is difficult since it is impractical to have hundreds to thousands of sample inlets to a single microfluidic device. Furthermore, the tubing used for supplying the samples to such a microfluidic device would already consume orders of magnitude more sample than is required for the actual analysis on the microfluidic device. So, there is a need for an efficient way to transport a large number of samples to a microfluidic device. Ideally such a sample transport system would be flexible enough to supply variable number of samples to a microfluidic device without any modifications in the transport system or the device.

The 'plug-in cartridge' technique developed by the Whitesides group[7] provides an elegant solution to the problem of introducing a large number of reagents on a microfluidic device through a single inlet. Under this approach, a series of sample plugs are loaded into a capillary, with air bubbles present between sample plugs acting as spacers. This capillary is connected to a microfluidic device, for serial delivery of these sample plugs. However, in this approach, the sample plugs are constantly in contact with the capillary inner surface, leading to the problem of cross contamination between plugs[7]. Another modification of this approach developed by the Ismagilov group[8] utilizes an immiscible carrier fluid instead of an air bubble to act as a spacer between sample plugs. The carrier fluid in this approach preferentially wets the inner surface of the capillary, thus preventing direct contact between sample plugs and the capillary surface. As a result, the problem of cross contamination between sample plugs is eliminated. The carrier fluids typically used for generating these sample plug arrays are fluorinated oils, which also reduce the problem of reagents leaking from sample plugs into the carrier fluid due to their low solubility for most reagents[8].

Although this approach is promising, the current techniques used under this approach for generating the 'sample plug cartridges' have some issues which need to be resolved. The common technique of using a syringe pump for aspirating sample plugs from a sample well[9-11] in a multi-well plate can be extremely slow. Another technique of using vacuum for aspirating a sample plug can be much faster[7]. However, this technique can only provide a maximum driving pressure of 1 atm (~15 psi). As a result, the driving force may not be sufficient to load large numbers of sample plugs into a capillary due to the increasing fluidic resistance of the capillary with the introduction of sample plugs. Furthermore, both of these techniques require the free end of the capillary to be attached to either a syringe or a vacuum source, thus excluding the possibility of operating this sample loading system in sync with the operations on a downstream microfluidic device. This can be a major setback to throughput as the possibility of conducting assays in continuous flow manner on microfluidic devices, as has been demonstrated earlier[12], is precluded. Therefore, there remains a need for improved systems and methods for screening large libraries of samples.

REFERENCES FOR BACKGROUND SECTION (1) Mayr, L. M.; Bojanic, D. Novel trends in high-throughput screening *Curr. Opin. Pharmacol.* 2009, 9, 580-588.
(2) Teh, S. Y.; Lin, R.; Hung, L. H.; Lee, A. P. Droplet microfluidics *Lab. Chip* 2008, 8, 198-220.
(3) Rane, T. D.; Puleo, C. M.; Liu, K. J.; Zhang, Y.; Lee, A. P.; Wang, T. H. Counting single molecules in sub-nanoliter droplets *Lab. Chip* 2010, 10, 161-164.
(4) Brouzes, E.; Medkova, M.; Savenelli, N.; Marran, D.; Twardowski, M.; Hutchison, J. B.; Rothberg, J. M.; Link, D. R.; Perrimon, N.; Samuels, M. L. Droplet microfluidic technology for single-cell high-throughput screening *Proc. Natl. Acad. Sci. U.S.A.* 2009, 106, 14195-14200.
(5) Kiss, M. M.; Ortoleva-Donnelly, L.; Beer, N. R.; Warner, J.; Bailey, C. G.; Colston, B. W.; Rothberg, J. M.; Link, D. R.; Leamon, J. H. High-throughput quantitative polymerase chain reaction in picoliter droplets *Anal. Chem.* 2008, 80, 8975-8981.
(6) Zhong, Q.; Bhattacharya, S.; Kotsopoulos, S.; Olson, J.; Taly, V.; Griffiths, A. D.; Link, D. R.; Larson, J. W. Multiplex digital PCR: breaking the one target per color barrier of quantitative PCR *Lab. Chip* 2011, 11, 2167-2174.
(7) Linder, V.; Sia, S. K.; Whitesides, G. M. Reagent-loaded cartridges for valveless and automated fluid delivery in microfluidic devices *Anal. Chem.* 2005, 77, 64-71.
(8) Chen, D. L.; Ismagilov, R. F. Microfluidic cartridges preloaded with nanoliter plugs of reagents: an alternative to 96-well plates for screening *Curr. Opin. Chem. Biol.* 2006, 10, 226-231.

(9) Zheng, B.; Ismagilov, R. F. A microfluidic approach for screening submicroliter volumes against multiple reagents by using preformed arrays of nanoliter plugs in a three-phase liquid/liquid/gas flow *Angew. Chem. Int. Ed Engl.* 2005, 44, 2520-2523.

(10) Adamson, D. N.; Mustafi, D.; Zhang, J. X.; Zheng, B.; Ismagilov, R. F. Production of arrays of chemically distinct nanoliter plugs via repeated splitting in microfluidic devices *Lab. Chip* 2006, 6, 1178-1186.

(11) Li, L.; Mustafi, D.; Fu, Q.; Tereshko, V.; Chen, D. L.; Tice, J. D.; Ismagilov, R. F. Nanoliter microfluidic hybrid method for simultaneous screening and optimization validated with crystallization of membrane proteins *Proc. Natl. Acad. Sci. U.S.A.* 2006, 103, 19243-19248.

(12) Zhang, Y.; Ozdemir, P. Microfluidic DNA amplification—a review *Anal. Chim. Acta* 2009, 638, 115-125.

(13) Abramoff, M. D.; Magalhaes, P. J.; Ram, S. J. Image Processing with ImageJ *Biophotonics International* 2004, 11, 36-42.

SUMMARY

A continuous throughput microfluidic system according to an embodiment of the current invention includes an input system configured to provide a sequential stream of sample plugs; a droplet generator arranged in fluid connection with the input system to receive the sequential stream of sample plugs and configured to provide an output stream of droplets; a droplet treatment system arranged in fluid connection with the droplet generator to receive the output stream of droplets in a sequential order and configured to provide a stream of treated droplets in the sequential order; a detection system arranged to obtain detection signals from the treated droplets in the sequential order; a control system configured to communicate with the input system, the droplet generator, and the droplet treatment system; and a data processing and storage system configured to communicate with the control system and the detection system. The control system is configured to control the input system in conjunction with the droplet generator and to provide information to the data processing and storage system that identifies each droplet of the output stream of droplets with a corresponding sample plug of the sequential stream of sample plugs. The control system further controls the droplet treatment system and provides information to the data processing and storage system that identifies a treatment applied to each droplet of the output stream of droplets, and the data processing and storage system receives the detection signals and calculates a property of each treated droplet and identifies a corresponding plug and treatment for each treated droplet based on the sequential order.

A method of screening a plurality of samples according to an embodiment of the current invention includes obtaining a sequential stream of sample plugs, generating a sequential stream of droplets from the sequential stream of sample plugs using a selectively controllable microfluidic system, adding at least one reagent from a plurality of reagents to each of the sequential stream of droplets in sequential order using the selectively controllable microfluidic system, and measuring at least one physical property of each of the sequential stream of droplets in the sequential order. Information concerning an identity of the plug from which each droplet of the sequential stream of droplets is generated and the at least one reagent added to each droplet is used to identify measured droplets based on the sequential order during the measuring.

A continuous throughput microfluidic system according to an embodiment of the current invention includes an input system configured to provide a sequential stream of sample plugs; a droplet generator arranged in fluid connection with the input system to receive the sequential stream of sample plugs and configured to provide an output stream of droplets; a droplet treatment system arranged in fluid connection with the droplet generator to receive the output stream of droplets in a sequential order and configured to provide a stream of treated droplets in the sequential order; a detection system arranged to obtain detection signals from the treated droplets in the sequential order; a control system configured to communicate with the input system, the droplet generator, and the droplet treatment system; and a data processing and storage system configured to communicate with the control system and the detection system.

BRIEF DESCRIPTION OF THE DRAWINGS

Further objectives and advantages will become apparent from a consideration of the description, drawings, and examples.

FIG. 3A; a) Schematic: A custom SSL system was designed which employs positive pressure to inject a sample plug into a microcapillary from a standard multi-well plate. A custom capillary adapter in the SSL system provides an interface between a microcapillary and a multi-well plate. This adapter can seal a well on the multi-well plate, thus generating a temporary pressure chamber inside the sample well. A pressure input on the adapter can then be used to apply controlled pressure to the fluid inside the sample well. This positive pressure drives a small plug of sample from the well into the microcapillary. Following this, the seal is broken and the multi-well plate is moved to seal another sample well with the capillary adapter. This sequence of steps is repeated to generate a sample library into the microcapillary. FIG. 3B: b) An image of a food dye sample plug array generated using the SSL system. Each sample plug is separated from each other by an immiscible carrier fluid.

FIG. 11A: a) Picture of the custom SSL system. The SSL system features: 1) a custom-made Capillary Adapter, 2) an automated Z-stage, 3) a 96-well plate, 4) Manual X and Y stages and 5) an Electronic Pressure Controller. FIG. 11B: b) A fluorescence image of sample plugs containing Lamda DNA stained with PicoGreen. These sample plugs were generated in a silica microcapillary using the SSL system, without any visual feedback during plug generation due to transparent nature of the sample. The image indicates high uniformity of the sample plugs despite lack of visual feedback: The lack of fluorescence background in the area between sample plugs (carrier fluid) also indicates minimal sticking of sample to the inner wall of the capillary preventing chances of cross contamination between sample plugs. c) A plot of sample plug volume versus duration of peak pressure application ($T_{peak}$) at constant peak pressure, ($P_{peak}$: 1 psi). The linear relationship between sample plug volume and $T_{peak}$ indicates the capability of our SSL system to vary sample plug volume in a predictable manner. The small error bars also indicate the uniformity of the sample plugs generated for identical loading conditions.

DETAILED DESCRIPTION

Figure 1:
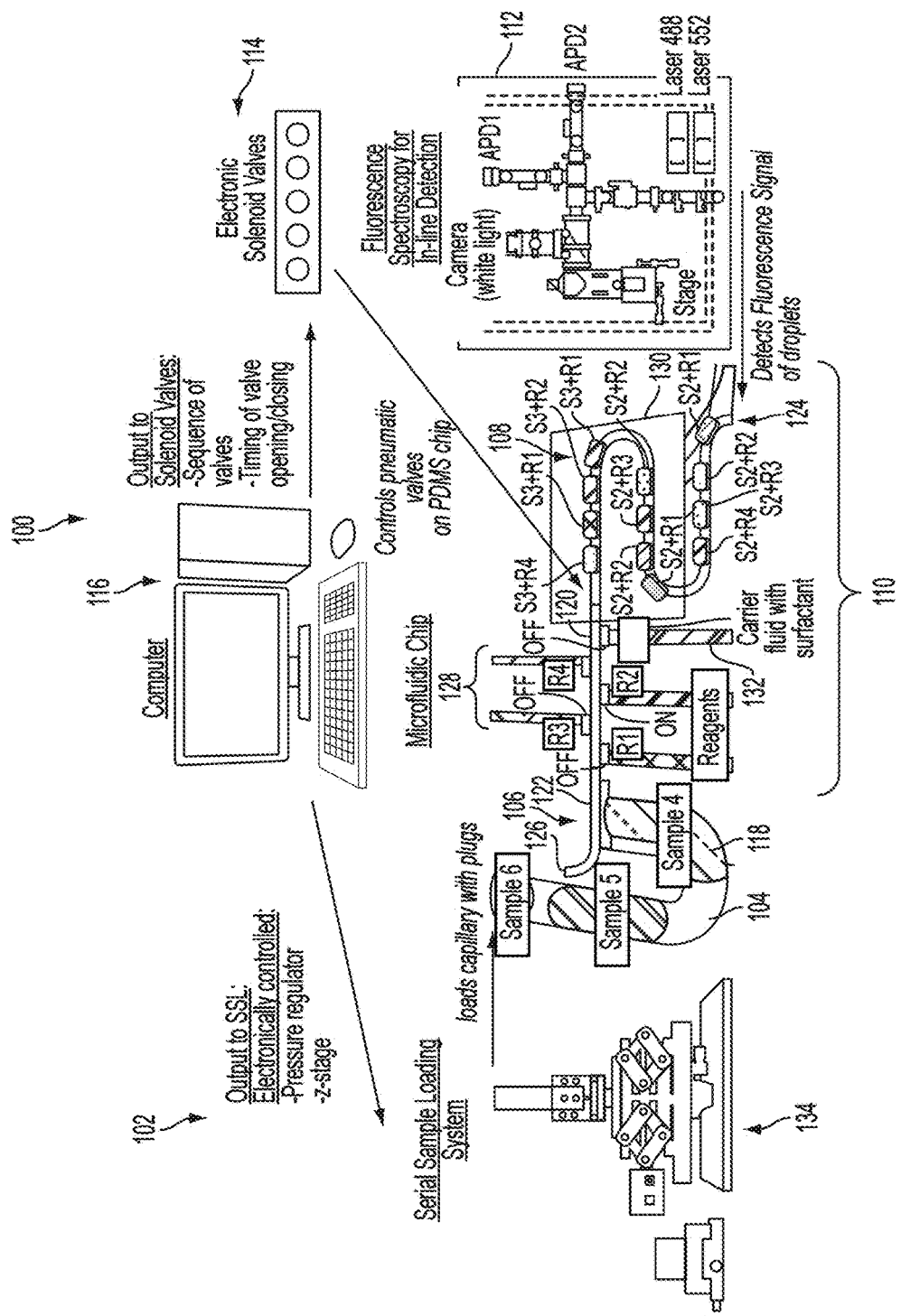
FIG. 1 is a schematic illustration of a continuous throughput microfluidic system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The aforementioned droplet platforms do not address the needs of numerous applications which require high degrees of multiplexing as well as high-throughput analysis of multiple samples. Some examples include, but are not limited to, genetic fingerprinting for forensics[14], single nucleotide polymorphism (SNP) analysis for crop improvement and domestication[15], genotyping required for identification of genes associated with common diseases[16] and generation of a blood donor genotype database for better matching between recipient and donor to prevent adverse transfusion reactions[17]. All of these applications require multiplexed screening of a single sample with a panel of reagents (or markers) and rapid screening of a large number of samples to generate the required databases.

In recent years, there have been attempts to expand the capacity of droplet platforms for the analysis of a biological or chemical sample with multiple reagents. One of the well-tested platforms has been the droplet platform developed by RainDance Technologies, for massively parallel PCR enrichment for DNA sequencing[18]. This platform involves a multistep approach with generation of a large library of PCR reagent droplets by a microchip, followed by merging of these reagent droplets with sample droplets generated from a DNA sample on a second device. These sample-reagent hybrid droplets are then collected in standard PCR tubes for thermocycling, followed by fluorescence detection and sequencing. In this platform, the content of each individual droplet is unknown and is decoded only by offline nucleic acid sequencing. Therefore, it cannot be applied to other applications that require real-time detection[4]. A solution to this problem is to associate a unique optical code with each reagent prior to mixing with the sample[19]. However, an optical-coding scheme based on fluorescence intensity is practically limited to a small number of 'codes' due to the small allowable number of fluorophores without spectral crosstalk and the limited dynamic range of the optical detection setup being used[4]. Furthermore, the electrocoalescence technique used in such platforms for droplet merging is susceptible to errors of no fusion caused by an excess of droplets of a reagent or unintended fusion of more than two droplets due to highly stringent synchronization requirements[20]. A recent article demonstrated a pico-injector which can overcome this problem and be used to add controlled volumes of multiple reagents to sample droplets using electromicrofluidics[21]. However, similar to droplet platforms discussed earlier, the content of each individual droplet is unknown unless a barcode is included in each individual droplet.

Alternatively, a series of articles adopted a cartridge technique for increasing the throughput of the droplet platform[22]. This technique involves generation of an array of reagent plugs in a capillary (cartridge), which are sequentially introduced into a simple microfluidic device for merging with a single substrate. The reagent plugs can be further digitized into smaller droplets prior to merging with the sample. As the length of the capillary can be very long, the number of reagents to screen against the sample is virtually limitless. This technique has been applied to many applications including protein crystallization[22] and study of bacterial susceptibility to antibiotics[23]. Although the aforementioned droplet and cartridge platforms are capable of high throughput and multiplexed analysis, they are still limited to screening of a single sample at a time.

Recently, a microfluidic platform was proposed for combinatorial chemical synthesis in picoliter droplets, where droplets of one library of reagents were fused at random with droplets containing a different set of reagents[20]. This platform has the potential of generating a large set of possible combinations of different reagents. However, as afore-discussed, the unknown identity of the compounds within individual droplets precludes its use for many screening applications that require real-time detection.

Some embodiments of the current invention provide a droplet platform capable of on-demand generation of nanoliter droplets of combinational mixtures of samples and reagents needed for biochemical screening applications that require multiplexing and high-throughput capability. On-demand droplet generation and manipulation using pneumatic valves has been demonstrated by other groups in the past[24-26]. However, these platforms have focused on generating multiple reagent combinations using fixed number of inputs to the device, severely limiting the number of possible sample-reagent combinations being generated on the device. The droplet platform according to some embodiments of the current invention uses a linear array of sample plugs as an input to the device, removing the limitation imposed by the number of inputs to the device. Initially, a preformed linear array of sample plugs separated by a carrier fluid is flowed from the cartridge into the microfluidic device, wherein each plug is digitized by a pneumatic valve into smaller sample daughter droplets. The volume of the resulting daughter droplet can be precisely controlled by varying the valve opening time and the back pressure on the cartridge containing sample plugs. The daughter droplets are then directly injected with reagents in a synchronization-free manner. The microfluidic design features a robust fusion module which exploits local channel geometry for synchronization-free injection of reagents into each sample daughter droplet. After reagent injection into a sample droplet, a microfluidic device according to some embodiments of the current invention introduces additional carrier fluid containing surfactant to the channel containing the sample-reagent hybrid droplet array to prevent unwanted merging of these droplets on the device. In an embodiment of the microfluidic device, droplets are indexed by their layout in a 1D array, enabling the identification of the contents of each droplet by spatial indexing. Spatial indexing as a means for identification of droplet content can obviate the need for a limiting optical barcoding scheme.

FIG. 1 is a schematic illustration of a continuous throughput microfluidic system 100 according to an embodiment of the current invention. The continuous throughput microfluidic system 100 includes an input system 102 configured to provide a sequential stream of sample plugs 104, a droplet generator 106 arranged in fluid connection with the input system 102 to receive the sequential stream of sample plugs 104. The term "plug" is used here to indicate that it is a larger volume than the droplets such that one plug can be used to generate a plurality of droplets. The general concepts of the current invention are not limited by a particular number of droplets produced from each plug. The droplet generator 106 is also configured to provide an output stream of droplets (not shown in FIG. 1). The continuous throughput microfluidic system 100 also includes a droplet treatment system 110 arranged in fluid connection with the droplet generator 106 to receive the output stream of droplets in a sequential order. The droplet generator 106 is also configured to provide a stream of treated droplets 108 in the sequential order, a few of which are illustrated in FIG. 1. The continuous throughput microfluidic system 100 also includes a detection system 112 arranged to obtain detection signals from the treated droplets in the sequential order. The continuous throughput microfluidic system 100 further includes a control system 114 configured to communicate with the input system 102, the droplet generator 106, and the droplet treatment system 110. The continuous throughput microfluidic system 100 also includes a data processing and storage system 116 configured to communicate with the control system 114 and the detection system 112.

The data processing and storage system 116 can be, but is not limited to, a programming computer, for example. The computer can be a localized computer, such as, but not limited to, a lap top computer, a desk top computer, or a workstation. However, the computer can also be a distributed system, such as a networked system of computers. The control system 114 can similarly have programming components implemented on the same of different computer as data processing and storage system 116. The data processing and storage system 116 and/or control system 114 can also include hard wired electronic components in addition to, or instead of software implemented functions.

The control system 114 is configured to control the input system 102 in conjunction with the droplet generator 106 and to provide information to the data processing and storage system 116 that identifies each droplet of the output stream of droplets with a corresponding sample plug of said sequential stream of sample plugs 104. The control system 114 further controls the droplet treatment system 110 and provides information to the data processing and storage system 116 that identifies a treatment applied to each droplet of the output stream of droplets. The data processing and storage system 116 receives the detection signals and calculates a property of each treated droplet and identifies a corresponding plug and treatment for each treated droplet based on the sequential order.

In some embodiments continuous throughput microfluidic system 100 can include a microfluidic chip 118 that defines a microfluidic channel 120 that includes an input end 122 configured to be fluidly connected to the input system 102. As illustrated in the example of FIG. 1, microfluidic channel 120 can have a first segment that is integrated with the droplet generator 106, a second segment that is integrated with the droplet treatment system 110, and a third segment that provides a measurement region 124 for the detection system 112. The term "microfluidic" channel means that the channel has cross-sectional dimensions that are less than one millimeter. For example, for an approximately circular cross-sectional channel, the channel diameter is less than one millimeter. For a square or rectangular cross-sectional channel, the channel height and width are both less than one millimeter. In some embodiments. The channel cross-sectional dimensions can be tens of microns, a few microns, or even less than one micron.

The microfluidic chip 118 can also be a multilayer microfluidic chip in some embodiments of the current invention. For example, the microfluidic chip 118 can include one or more channel layers, and one or more control layers to hydraulically and/or pneumatically control valves that can be incorporated with the microfluidic chip 118. The microfluidic chip 118 can have multiple sections for performing multiple functions, as is illustrated in FIG. 1. However, other embodiments could combine two or more microfluidic chips for performing the desired functions without departing from the broad concepts of the current invention.

The microfluidic chip 118 in the embodiment of FIG. 1 further defines a valve assembly 125 as a component of the droplet generator 106 that is selectively controllable by the control system 114. The droplet generator 106 also includes a fluid channel 126 for receiving carrier fluid to be input into the microfluidic channel 120 between adjacent droplets. The treatment system 110 can include a reagent adding section 128 and at least one of a reaction section or an incubation section 130, for example. The treatment system 110 can include additional and/or alternative functional units than those described in the example of FIG. 1.

The reagent adding section 128 includes a plurality of reagent input channels and corresponding valve assemblies configured to communicate with the control system such that one or more reagents can be selectively added to a selected droplet when the droplet is in the second segment of the microfluidic channel within the reagent adding section at a selected time. The example of FIG. 1 shows four reagent channels and corresponding valve assemblies. However, the broad concepts of the invention are not limited to a particular number of reagent channels. Alternatively, one, two or three could be used, or more than four could be used. In some cases, many more than four can be used. For example, tens or even hundreds could be included.

The reagent adding section 128 includes a portion of the microfluidic channel 120 in which a cross-section area is decreased relative to adjacent sections to stretch droplets across at least some of the plurality of reagent input channels. Some examples of a droplet stretching segment of the channel are described in more detail below. The reagent adding section 128 further includes a stabilizing-fluid input channel 132 and a corresponding valve assembly configured to communicate with the control system 114 such that a stabilizing fluid containing a surfactant can be selectively added to droplets within the droplet treatment system. The stabilizing fluid can be a carrier fluid such as that used to separate the plugs and droplets with the addition of a surfactant, for example. The stabilizing-fluid input channel 132 is arranged downstream from the plurality of reagent input channels 128 such that droplets can be stabilized after addition of reagent. In many applications, one of the plurality of reagents will be added. However, the broad concepts of the current invention are not limited to that example. Any combination of two or more of the available reagents could be added, if desired for a particular application.

In some embodiments, the reaction section or incubation section 130 includes a temperature control component. For example, the shaded area could be a Peltier component to heat and/or cool the reaction or incubation section. Other temperature control components could also be used, such as, but not limited to, resistive heating elements and/or heat conduction component's that are in thermal contact with external heat sources or heat sinks. The temperature control component can also be adapted to communicate with the control system. This can permit maintaining a constant temperature and/or providing a programmed temperature profile, either spatially along the microfluidic channel 120 and/or changing with time. Furthermore the microfluidic channel can have a serpentine path in the reaction section or incubation section 130 to allow for a compact arrangement with an extended path length. In some embodiments, as in some examples described in more detail below, the reaction section or incubation section 130 is an incubation section.

In some embodiments, the input system 102 includes a capillary tube 104 that is suitable to be loaded with the sequential stream of sample plugs with separation fluid between adjacent sample plugs. For example, a silica capillary tube could be used in some embodiments. However, the broad concepts of the current invention are not limited to this example. For example, without limitation, other cartridge or tube structures could be used.

As will be described in more detail below in reference to particular examples, capillary tube 104 of the input system 102 has a cross-sectional opening that extends beyond a cross-sectional opening of the input end 122 of the microfluidic channel 120. The input system 102 can further include an adapter that has a first end that substantially matches the cross-sectional opening of the capillary tube 104 and a second end that substantially matches the cross-sectional opening of the input end 122 of the microfluidic channel 120. In some embodiments, the adapter has a substantially smooth inner surface that tapers from the first end to the second end. In alternative embodiments, the adapter has a segmented inner surface that provides a plurality of steps to transition from the first end to the second end.

In some embodiments, the input system 102 can further include an automated sample loader 134 configured to load the capillary tube 104 with the sequential stream of sample plugs and with carrier fluid between adjacent sample plugs from a multi well plate and to deliver and fluidly connect the capillary tube and the adapter to the input end 122 of the microfluidic channel 120. In some embodiments, the automated sample loader 134 can have a linear three-axis stage to move the multi well plate while maintaining the capillary tube 104 fixed. Moving the multi well plate instead of the capillary tube 104 can be advantageous in some applications to prevent disturbing sample as it is being loaded. However, the capillary tube 104 could be moved instead of, or in addition to, the multi well plate in some embodiments.

The detection system 112 can be, or can include, an optical system. However, other embodiments can include additional or alternatives to optical systems. The optical system can be, but is not limited to, a fluorescence spectroscopy system.

The control system 114 can be configured to selectively, start, stop and regulate a flow speed of the output stream of droplets and the stream of treated droplets, for example.

Figure 2:
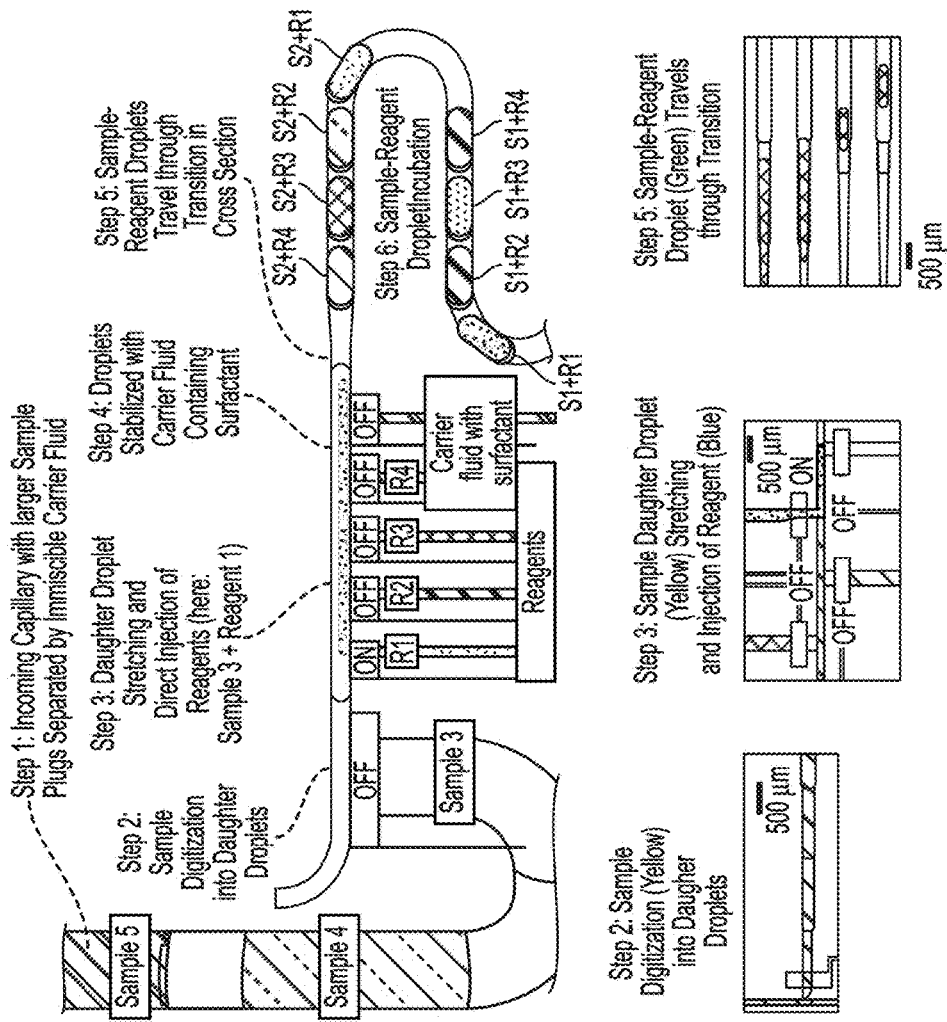
FIG. 2 is a schematic illustration of the sample screening platform of the embodiment of FIG. 1. Step 1: A cartridge is loaded with a library of sample plugs separated by an immiscible carrier fluid. This cartridge is interfaced with a microfluidic device. Step 2: On-demand digitization of incoming sample plugs into smaller daughter droplets. The volume of individual daughter droplets can be controlled by valve opening time and back pressure on the cartridge. Step 3: By exploiting the cross sectional area of the central channel, the sample daughter droplet is stretched in the "Fusion Region". This approach allows for robust, synchronization-free injection of up to four reagents simultaneously directly into the daughter droplet. The volume of reagent injected is controlled through modulation of back pressure and valve opening time corresponding to the reagent inlet. Step 4: Once sample and reagent have been combined into one droplet, the droplets are stabilized with carrier fluid containing surfactant to prevent unwanted droplet coalescence downstream. Step 5: Sample-reagent droplets travel to an incubation channel. Step 6: The sample-reagent droplets are incubated while maintaining their sequence in downstream incubation channels. This approach allows for droplet identification through spatial indexing in a 1-Dimensional array.

In operation of the continuous throughput microfluidic system 100, the input system 102 loads a sequential stream of sample plugs 104 in a particular order as regulated and recorded by the control system 114 and the data processing and storage system. The droplet generator 106 receives the sequential stream of sample plugs 104 from the input system 102 and generates a plurality of droplets from each plug to provide a stream of droplets ordered in accordance with the order generated from the respective plug. (FIG. 2 provides a schematic illustration describing operation the system 100.) This sequence, thus provide a linear array of droplets which can then be processed in a manner analogous to an assembly line. The identities and subsequent processing of each droplet is known as corresponding to the place within the linear array. For example, the first droplet generated, will be the first droplet measured at the end; and the one-hundredth droplet generated will be the one-hundredth droplet measured and the end. The processing along the way is also known. For example when one or more reagents are added to a particular droplet in reagent adding section 128, the droplet enters a constricted region to stretch the droplet across multiple reagent channels. For example, the droplet can be stretched to extend across all reagent channels in some embodiments. The control system can then stop the "assembly line" such that the stretch droplet is held for a desired period of time in which to effect the addition of the one or more reagents. The "assembly line" can then be restarted to bring another droplet into the constricted region to be stretched across the reagent channels. This process can be continue in a "continuous" manner. The term "continuous" is intended to mean that there is not a finite specific number of droplets that can be processed. The assembly line can be started and run as long as is desired in a particular application. In addition, the droplets can be generated and processed on demand under control of the control system 114. In addition, once the assembly line is started, the system has very high throughput since it is a continuous stream.

Although the embodiment described above has one microfluidic channel 120, other embodiments can include multiple systems operating in parallel to further increase throughput. Since the system is a microfluidic system, some embodiments can include large numbers of such systems in parallel. For example, there could be tens, hundreds, or even thousands of such systems operating in parallel.

The following examples describe some embodiments and some applications in more detail. However, the broad concepts of the current invention are not limited to the particular examples.

EXAMPLES

Materials and Methods
Serial Sampling Loading System

Figures 3A, 3B:
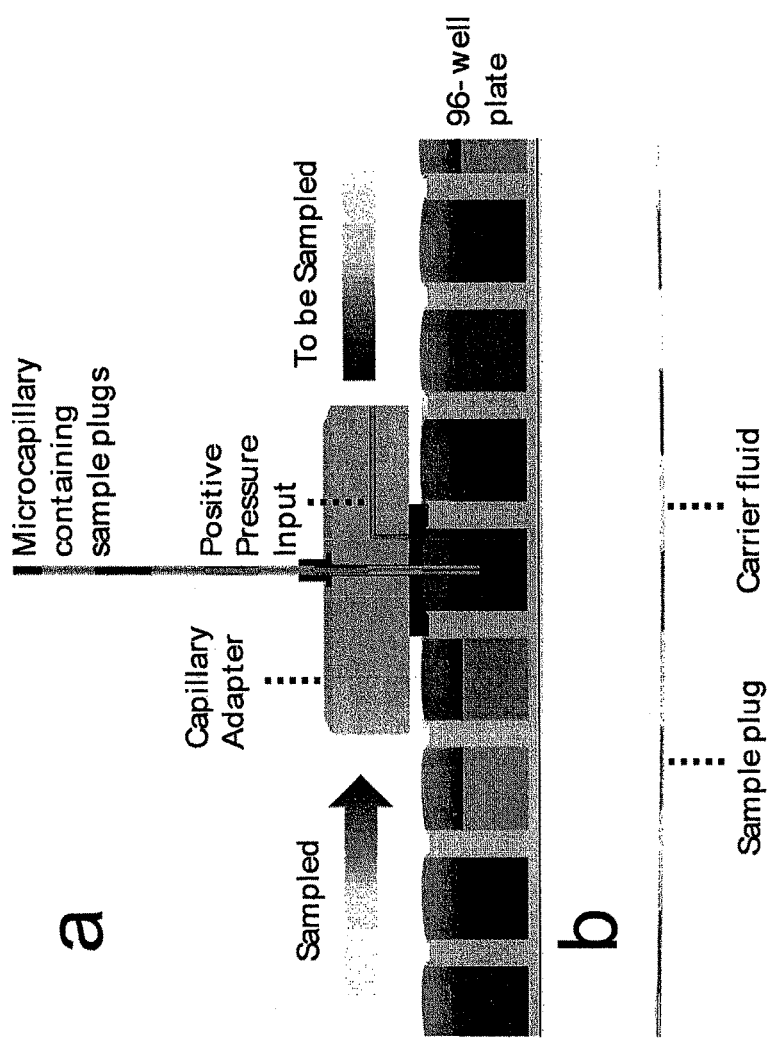
FIGS. 3A and 3B illustrate a 'Serial Sample Loading' (SSL) system according to an embodiment of the current invention.

The sample library was generated using a custom-designed Serial Sample Loading System (SSL). FIG. 3A is a schematic illustrating the functioning of the SSL system. Briefly, the SSL system was designed to be compatible with Costar 96-well plates (Corning). Initially the wells on a Costar 96-well plate are filled with the samples and the carrier fluid to be used for generating the sample plug array. An Aquapel (PPG Industries) treated silica capillary is then attached to a capillary adapter on the SSL system, which is also connected to a positive pressure input. A sample well is then interfaced with the capillary through the capillary adapter. Application of positive pressure to the sealed sample well for a controlled amount of time is then used to drive a sample plug from the well into the capillary. This sequence of steps is then repeated to load alternating sample and carrier fluid plugs into the capillary (FIG. 3B). More detailed information on the structure and operation of different components of the SSL system can be found below.

Fabrication of the Master Molds for the Microfluidic Device

Figures 4A, 4B:
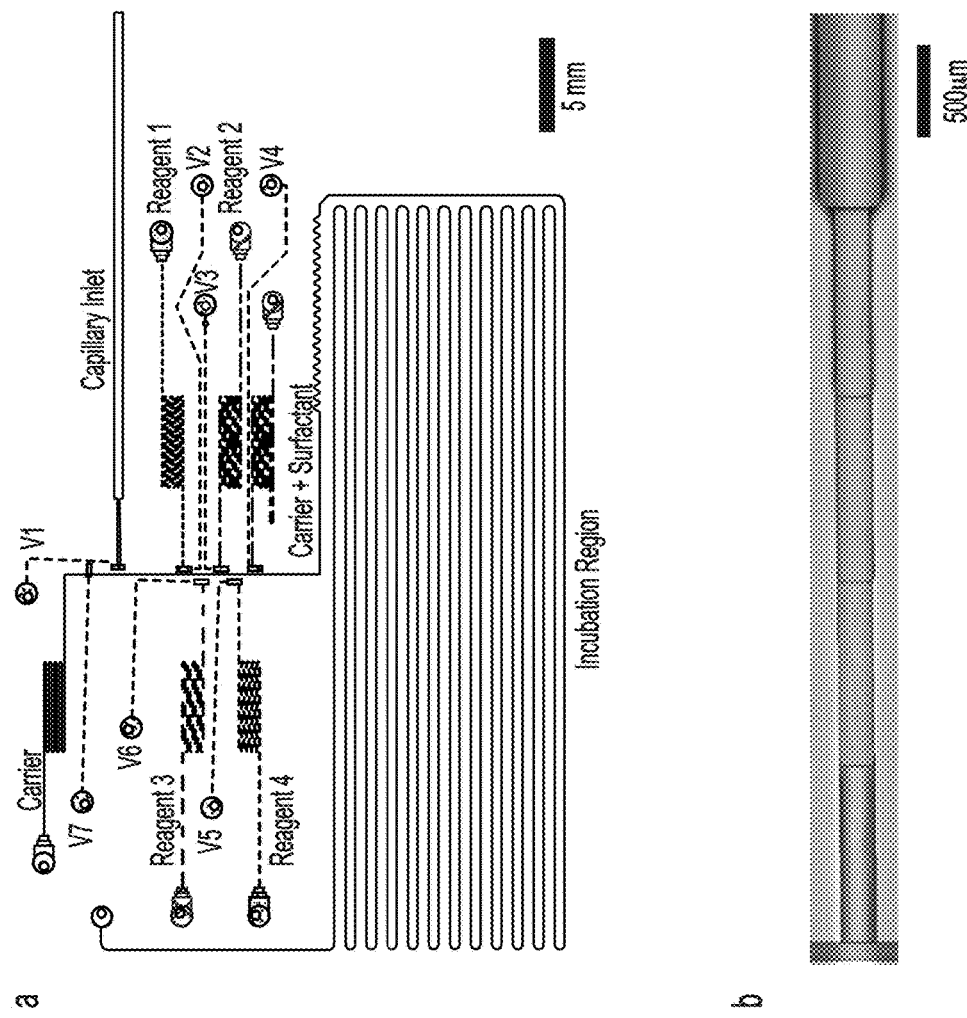
FIGS. 4A and 4B show an example of a microfluidic chip according to an embodiment of the current invention, a) Photograph of a prototype device. The microfluidic device has a multichannel architecture: 1) The central channel with fusion region and incubation region (purple), 2) Capillary inlet, 3) Reagent inlets: reagent 1 (pink), reagent 2 (orange), reagent 3 (green), reagent 4 (turquoise) and surfactant oil inlet (yellow). The valves on the device (V1-V7) are indicated by a turquoise dye. b) A scan of the capillary inlet region, indicating the height difference between different sections of the capillary inlet to facilitate smooth sample plug transition from the large ID of the capillary to the shallow channels on the microfluidic device.
Figure 8:
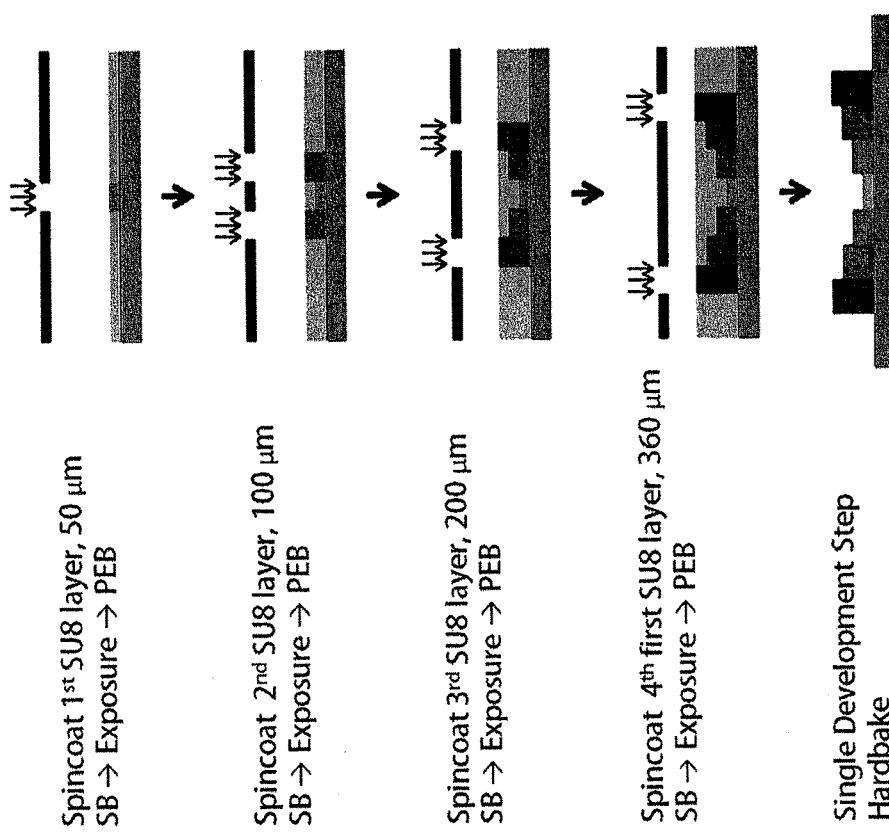
FIG. 8 illustrates a microfabrication process with single developing step. Four consecutive layers of SU8 photoresist are spin coated and patterned on a single silicon wafer using photolithography. Each layer undergoes all standard photolithography steps like soft bake (SB), exposure and post-exposure bake (PEB). However, the developing step is conducted in common for all layers after patterning the last photoresist layer.

The fluidic layer on the microfluidic device features five different heights of microfluidic channels (FIG. 4B). As a result, the fluidic mold consists of five different layers of photoresist. The fluidic channel heights in these five different photoresist layers were expected to be 25 µm, 50 µm, 100 µm, 200 µm and 360 µm. The photoresist used for the 25 µm layer was SPR 220-7.0 (Rohm & Haas), while the rest of the layers were fabricated using SU-8 3050 (MicroChem). Fabrication was performed using standard photolithography techniques. Briefly, a SPR 220-7.0 layer was spin coated on a 4 inch silicon wafer. This layer was patterned using photolithography and hard baked to generate a rounded channel cross section, required for effective valve closure, as has been described earlier[27]. For all other layers, SU-8 3050 was spin-coated on the wafer and patterned using standard photolithography, excluding the developing step. This technique was found to be very effective in preventing generation of bubbles and non-uniform coating of photoresist on the wafer due to the presence of features from earlier layers on the wafer. A single developing step for all four SU-8 3050 layers was used to remove excess photoresist on the wafer (FIG. 8). The control layer for the microfluidic device on the other hand consisted of microfluidic channels of a single height. As a result, the mold fabrication for the control layer was relatively simpler, with a, single layer of SU-8 3050 photoresist, 50 µm in height.

Microfluidic Device Fabrication

Figure 9:
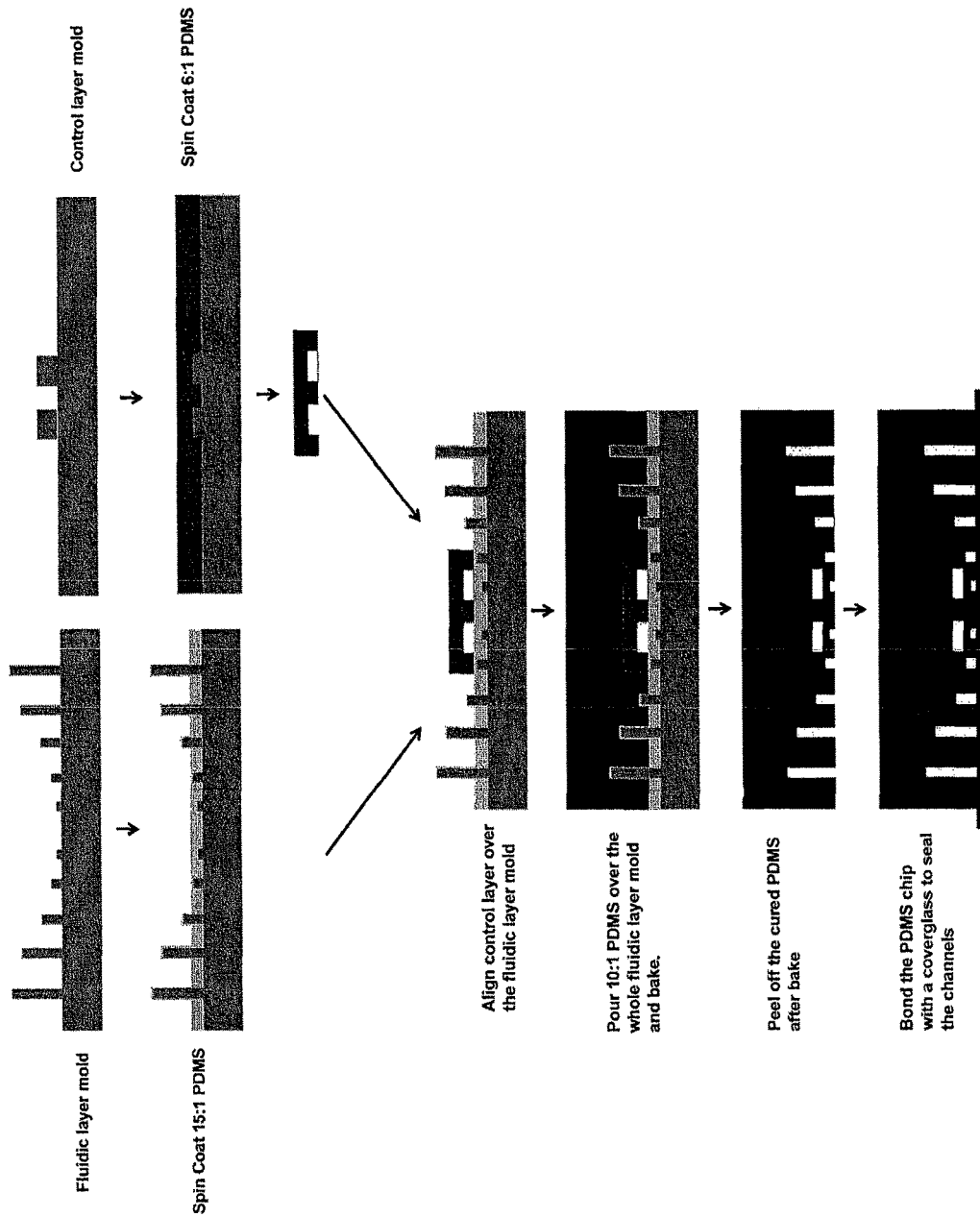
FIG. 9 is an illustration of a modified microfluidic device fabrication: The process flow used for fabrication of our microfluidic devices to accommodate tall channels in the fluidic layer while maintaining the functionality of push-down valves. (6:1, 10:1 and 15:1 refer to the ratio of the base to curing agent used to mix a batch of PDMS)

The microfluidic devices were fabricated using multilayer soft lithography techniques[27]. The protocol differed slightly from our standard protocol[28-30] due to the need for proper functioning of push-down valves[31] while accommodating tall features (up to 360 µm) on the fluidic layer. The thickness of the polydimethylsiloxane (PDMS) membrane separating the control layer and the fluidic layer in a microfluidic device needs to be less than ~50 µm for complete valve closure at reasonable pressure (~30 PSI). However, the presence of fluidic regions as tall as 360 μm on the fluidic layer mold precluded the possibility of covering the entire fluidic layer mold with PDMS, while maintaining the thickness of the PDMS layer to a value less than 50 μm in the regions of the device containing valves. To overcome this problem, a modified three-layer fabrication process was developed. Detailed description of the fabrication process is included below (FIG. 9).

Capillary-to-Chip Interface

Following the microfluidic device fabrication, a silica capillary was attached to the 'capillary inlet' on the microfluidic device (FIG. 4B). The 360 μm tall channel region at the capillary inlet accommodates a silica capillary with an OD of 360 μm. A 10 mm section of silica capillary is inserted horizontally into this tall channel on the device until it is flush with the 200 μm tall fluidic channel on the device. To seal the capillary to the chip and prevent leakage, PDMS was dispensed around the capillary at the interface between the capillary and the device. The PDMS tended to crawl into the 360 μm channel and surround the capillary, effectively sealing the capillary-to-chip connection. The final assembly was baked for at least 2 hours at 80° C. before usage.

Device Control

All the inputs on the device were kept under constant pressure, with independent input pressure for 1) carrier fluid input, 2) all four reagent inputs and 3) carrier fluid with surfactant input. The pressure applied to the capillary input was controlled directly by the pressure controller used for the SSL system. All the valves on the device were controlled by an array of off-chip solenoid valves, as has been demonstrated earlier[28]. We developed Matlab (Mathworks, Natick Mass.) software for computer control of the valve array. This software allowed us to execute a predetermined sequence of valve actuation with independent time control for each actuation. The opening of a valve corresponding to an input on the device led to the release of a droplet of fluid from that inlet into a central channel on the device. The volume of this droplet could be controlled through variation of the opening time of the valve.

Reagents

All the devices and capillaries were treated with Aquapel to render their surface hydrophobic. The testing of our platform was performed using food dyes (Ateco, Glen Cove, N.Y.) to mimic different samples and reagents for easy visualization. The carrier fluid used to maintain the separation between sample plugs consisted of a perfluorocarbon (FC-3283) and a non-ionic fluorous-soluble surfactant (1H, 1H,2H,2H-Perfluoro-1-octanol) mixed in a ratio of 8:1 by volume. The carrier fluid with surfactant consisted of FC-40 (3M) and 2% 'EA' surfactant (Raindance Technologies) by weight.

Sample Plug and Droplet Volume Estimation

We estimated the volume of sample plugs and sample droplets generated using the SSL system and the microfluidic device respectively. This volume estimation was performed by processing the images of these sample plugs or droplets using the software ImageJ[32]. Specifically, for sample plug volume estimation, a series of sample (blue food dye) plugs were generated in a silica capillary using the SSL system. A color image of these plugs was taken against the white background of a 'letter' sized sheet of paper using a standard Digital Single-Lens Reflex (DSLR) camera. This image was imported in ImageJ and the length scale was set to true length using the known length of the letter sized paper in the image. The lengths of the sample plugs were then manually measured for each plug using the 'Measure' function in ImageJ. The plug lengths could be converted to plug volumes with the known cross sectional area of the capillary.

For sample droplet volume estimation, we generated droplets made of blue food dye using one of the four reagent inlets on the microfluidic device, until the whole incubation region on the device was full of droplets. The whole device was then imaged using a DSLR camera. The image was imported in ImageJ and cropped to obtain an image of the incubation region on the device. This image was then converted to a binary image using color thresholding to identify droplets over the background image. An estimate of the droplet area for each droplet in the image was then obtained using the 'Analyze Particles' function. This analysis was limited to particle areas larger than a lower threshold to exclude any particles and occasional satellite droplets from the analysis. The droplet areas thus estimated were then converted to droplet volume using the known depth of the incubation channel region (200 μm).

Results and Discussion

Overall Work Flow

FIG. 2 is a schematic illustrating the functioning of the platform. Initially a cartridge (capillary) is loaded with a library of sample plugs forming a serial sample plug array: plugs are separated from each other by an immiscible carrier fluid. This cartridge is interfaced with a microfluidic device featuring multichannel architecture and pneumatic microvalves. The microfluidic device digitizes sample plugs into smaller daughter droplets. Each sample daughter droplet then moves to the downstream fusion region where a specific reagent is injected into the sample daughter droplet. The reagent droplets are injected into the sample daughter droplet through controlled actuation of valves corresponding to the reagent inlets. No strict synchronization or droplet detection module is necessary for fusion of sample and reagent to occur as the sample droplet is elongated in the fusion area exploiting the local channel geometry. The resulting sample-reagent droplet undergoes mixing and travels downstream to the incubation region on the device. After reagent injection, additional carrier fluid containing surfactant is released into the central channel on the device to stabilize sample-reagent hybrid droplets. The sequence of droplets is maintained throughout the device, precluding the need for a complicated barcoding scheme to identify the contents of each individual droplet.

Capillary-to-Chip Interface

Our prototype platform necessitated the capillary-to-chip interface design to allow for sample plug introduction on chip. This objective presented a unique challenge, since proper functioning of the platform requires smooth transition of sample plugs from the large ID of the capillary to shallow channels on the device in the valve regions. There have been demonstrations of capillary-to-chip interfaces in the past for introducing sample plugs from a capillary to a microfluidic device. However, the devices used don't face this problem as they typically feature large channels with a valveless design[22,23]. The capillary interface we designed (FIG. 4B) between the capillary and microfluidic chip was found to be effective in minimizing plug break up as plugs moved from the high ID (200 μm)μm) of the capillary to the shallow channels on chip (25 μm). This transition consisted of 5 different channel sections with gradually reducing channel heights of 360 μm, 200 μm, 100 μm, 50 μm and 25 μm. This gradual transition minimizes the shear stress on the sample plug as it traverses from a capillary to the shallow channels on the chip, preventing its breakup in transit.

Droplet Uniformity Using Mechanical Valve Based Droplet Generation

Figures 5A, 5B:
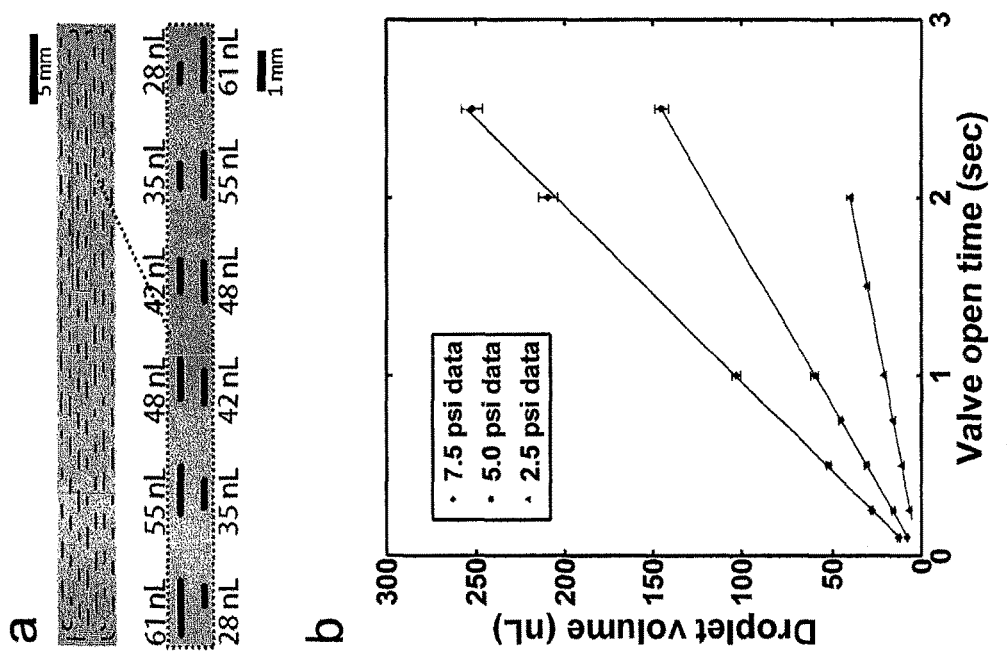
FIGS. 5A and 5B provide results for control of droplet volume and droplet uniformity using mechanical valve based droplet generation. a) Micrograph of the incubation region on the microfluidic device filled with reagent droplets generated using sequentially increasing valve opening times ($T_{on}$=0.3, 0.4, 0.5, 0.6, 0.7, 0.8 seconds) for a fixed back pressure on the reagent inlet ($P_{reagent}$=5 psi). This resulted in a linear array of repeats of a sequence of six droplets, with each droplet increasing in volume. b) A plot of droplet volume versus the valve opening time ($T_{on}$) for a valve corresponding to a reagent inlet for three different values of back pressures applied to the reagent inlet ($P_{reagent}$=2.5, 5 and 7.5 psi). The droplet volumes plotted are an average of volumes estimated from 50 droplets for each condition. The error bars in the volume data are too small to be seen on the plot.

We examined the performance of the mechanical valves on our microfluidic device for their capability to control the droplet size generated. To conduct this experiment, we primed the incubation channel on the device with the carrier fluid. We then used one of the reagent inlets on the device for generating droplets made of blue-colored food dye into the incubation channel region. The two parameters which could be used to control the droplet size generated from a reagent inlet, are 1) Input pressure to the reagent inlet ($P_{reagent}$) and 2) The opening time of the valve corresponding to the reagent inlet ($T_{open}$). Initially, we fixed the value of $P_{reagent}$ and generated droplets on the device for different values of $T_{open}$. Droplet generation was continued for each condition tested until the incubation region on the device was completely full of droplets. We then estimated the volume for all these droplets using the image processing technique discussed in the 'Materials and Methods' section. The mean and standard deviation of fifty droplets generated for each condition was plotted against $T_{open}$ in FIG. 5B. This experiment was repeated for three different fixed values of $P_{reagent}$. As expected, the linear relationship between droplet volume and $T_{open}$ indicates excellent and predictable control of the device over droplet volume. Small standard deviation observed on the droplet volume also indicates excellent droplet uniformity for identical droplet generation conditions. This result is very important to ensure the capability of the device to generate droplets of various compositions on-demand.

Sample Digitization

Figures 7A, 7B:
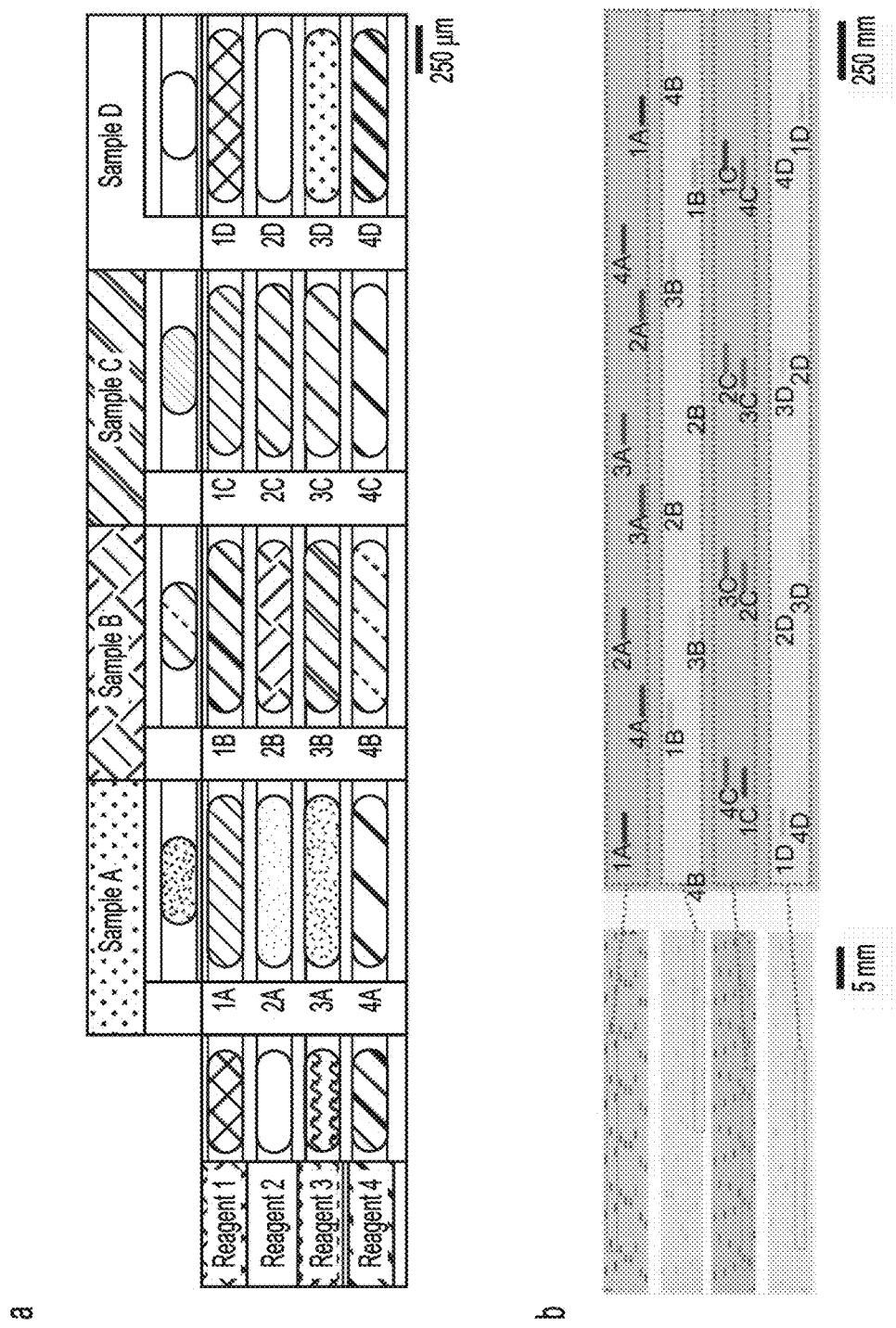
FIGS. 7A and 7B show photographs of the incubation region indicating multiplexing capability of the device, a) Table with micrographs indicating combinatorial mixture droplets generated on the device using four different samples [Sample A (blue), Sample B (yellow), Sample C (green), Sample D (water)] and four different reagents [Reagent 1 (orange), Reagent 2 (water), Reagent 3 (light, blue), Reagent 4 (yellow)]. Droplets 1A-4A, 1B-4B, 1C-4C, and 1D-4D are each generated from a combination of the sample and reagent in the corresponding column and row respectively. For example, Droplet 1A is the combination of sample A with reagent 1. b) Left panel shows four different micrographs showing repeating sequences of sample daughter droplets generated from a single sample plug merged with four different reagents on a single device. The right panel shows zoomed in version of a small section of the micrographs from the left panel for easy visualization of the droplet sequence. The droplet identification codes in this panel are the same as those used in subfigure a. Note: The sequence of droplets seems to be going in opposite direction in alternate channels due to the changing direction of flow in serpentine channels.

We examined the capability of our device to digitize a set of sample plugs being supplied to the device into smaller sample daughter droplets. To conduct this experiment, we generated a set of sample plugs into a silica capillary using the SSL system. These sample plugs were delivered to the microfluidic device through the capillary inlet, under pressure provided by the pressure controller on the SSL system. For this experiment, the repeating sequence of steps executed on the device was as follows: 1) Generate small droplet from a sample plug in the central channel, 2) Move the droplet towards incubation region with carrier fluid 3) Release small amount of carrier fluid with surfactant in the central channel. Repeating this set of steps led to generation of an array of sample droplets generated through digitization of sample plugs on the device. Examples of unmerged sample daughter droplets are shown in FIG. 7A (Sample droplets A, B, C and D). The order of the sample plugs in the capillary is consistently maintained on the device, even after the digitization operation. One shortcoming of this operation is the generation of non-uniform droplets towards the beginning and the end of the sample plugs. This is because the valve actuation sequence is continuously executed without any sensing of sample plug arrival on the device. However, the sample droplet uniformity is maintained throughout the rest of the sample plug. As the droplets generated on the device are stabilized with surfactant, undesirable merging of non-uniform droplets originating from the front- or back-end of plugs is avoided on the device.

Generation of Droplets of Combinatorial Mixtures

Figures 6A, 6B:
FIGS. 6A and 6B provide a demonstration of reagent injection in sample daughter droplets merging with reagents. a) Time series of images indicating reagent injection into sample daughter droplets at the 'Fusion zone' on the device. A sample daughter droplet (yellow) is released from the capillary inlet and is halted in the 'Fusion zone' by actuating a valve upstream which controls carrier fluid injection into the central channel on the device. A reagent (blue) is released and injected directly into the sample droplet. The elongated configuration of the sample daughter droplet in the 'Fusion zone' ensures robust reagent injection operation on the device without the need for precise sample droplet positioning. b) A series of photographs demonstrating injection of different numbers of reagents into a sample daughter droplet simultaneously.

In this section we demonstrate an example of generation of combinatorial mixtures from sample plugs and reagent droplets on our device according to an embodiment of the current invention. For discernibility, we chose to use different food dye solutions to simulate different samples and reagents. FIGS. 6A and 6B show how reagent injection operations are performed in the fusion region on an embodiment of our device. First, a sample plug travels from the capillary on to the microfluidic device. This plug is then chopped into a smaller sample daughter droplet. This droplet is then moved to the downstream fusion zone through release of carrier fluid in the central channel on the device. As every single input on the device is controlled with an individual valve, the device functions like an assembly line with complete temporal and spatial control over every single operation, as against typical droplet generating devices where the carried fluid flow is continuous. This level of control also implies that the operation of the device can be paused and resumed with a completely new valve actuation sequence on demand without affecting the existing droplets on the device. None of the droplet devices reported in literature so far has this capability to the best of our knowledge. A reagent droplet is then injected directly into the sample daughter droplet (FIG. 6A). The volume of reagent solution injected into the sample droplet can be controlled through variation of the opening time for the valve corresponding to the reagent inlet. The fusion zone is designed such that the sample daughter droplet is sufficiently elongated within a region, which overlaps with all the injection ports of the interrogating reagents. This elongated droplet state removes the need for strict positioning accuracy requirements on the sample droplet for reliable injection of reagent into the sample droplet. In addition to demonstrating injection of a single reagent in a sample droplet, we have demonstrated injection of up to four reagents into a single sample droplet as shown in FIG. 6B. The concept of droplet elongation to aid reagent injection can be easily scaled to accommodate tens of reagent inlets, if desired. Post reagent injection, no unwanted mixing of reagents was observed with subsequent sample plugs. Occasional residual reagents residing between the activated valve and central channel at a reagent inlet are encapsulated by a sheath of carrier fluid which prevents fusion with the next sample droplet.

After reagent injection, the sample-reagent droplet is driven further downstream with the help of carrier fluid. Following this, a small plug of carrier fluid with surfactant is released in the central channel for stabilizing the droplets in the incubation region. Using this scheme we can simultaneously take advantage of a surfactant-free zone in one area of the chip to promote sample-reagent merging while deliberately using surfactant in another area to increase droplet stability and prevent unwanted droplet merging. In addition, the backpressure on the carrier fluid inlets was used to control flow velocity of the droplets. For the results presented in this paper, the flow velocity of droplets was ~5 mm/second. However, the flow velocity can be easily tuned by controlling the back pressure on the central carrier fluid channel.

FIGS. 7A and 7B demonstrate the reliability of the fusion mechanism on our device. FIG. 7A is a table of 16 different sample-reagent combinations generated on a single chip through all possible merging combinations of four different sample daughter droplets (A: blue, B: yellow, C: green, D: water) with four different reagents (Reagent 1: orange, Reagent 2: water; Reagent 3: blue, Reagent 4: yellow) with the condition of merging exactly one sample with one reagent.

The micrographs in FIG. 7B show a repeating sequence of the sample-reagent hybrid droplets in the incubation region of the chip. The chip is operated such that the sample daughter droplets are merged with a repeating sequence of four different reagents. As a result a repeating sequence of four possible combinations generated through mixing a single sample with four different reagents can be seen in each individual micrograph. Once a sample plug is exhausted, the sample daughter droplets generated from the next incoming sample plug start merging with the same repeating sequence of reagents generating a repeating sequence of a new set of four different sample-reagent combinations in the incubation region on the chip.

The droplet monodispersity as well as the uniform spacing between droplets is clearly visible in these micrographs. The inset in FIG. 7B displays zoomed-in view of these micrographs of the incubation region illustrating two repeats of each sequence in the incubation region. These images also demonstrate the capability of the device to maintain the order in which droplets are generated throughout the incubation region on the device. We have demonstrated 16 combinations in this instance, but by employing multiple (2, 3 or 4) reagent merging with sample daughter droplets, as demonstrated in FIG. 6B, many more combinations can be generated using our device.

Mold Fabrication

The work flow used for fabricating the fluidic layer mold is illustrated in FIG. 8. The mold consists of five different layers of photoresist with heights of 25 µm, 50 µm, 100 µm, 200 µm and 360 µm. The photoresist used for the 25 µm layer was SPR 220-7.0 (Rohm & Haas), while the rest of the layers were fabricated using SU-8 3050 (MicroChem). Initially a 25 µm tall SPR 220-7.0 layer was spin coated on a silicon wafer. This layer was patterned using photolithography and hard baked to generate a rounded channel cross section, required for effective valve closure. The rest of the layers were fabricated by stacking and patterning multiple layers of SU-8 3050 on the wafer. All of the steps required for standard photolithography (Soft Bake, Exposure and Post Exposure Bake) are conducted for each layer of SU-8 3050, except for the developing step. This step is conducted in common for all layers after the last SU-8 layer is patterned to remove excess unexposed photoresist from the wafer (FIG. 8). This technique was found to be very effective in preventing generation of bubbles and non-uniform coating of photoresist on the wafer due to the presence of features from earlier layers on the wafer.

Device Fabrication and Operation

The microfluidic device for our experiments was fabricated using multilayer soft lithography technique. Standard dual layer microfluidic devices with push-down valves fabricated using polydimethylsiloxane (PDMS) require shallow fluidic channels to make sure the layer of PDMS between the fluidic and control layer is sufficiently thin (~50 µm) for complete closure of valves at low pressures (<30 psi). The requirement of shallow fluidic channels is incompatible with our chip design. So we developed a modified fabrication process for our device. This modified soft lithography process is outlined in FIG. 9. For this modified fabrication process, three different batches of PDMS were mixed. These varied in composition, and base to crosslinking agent ratios of 15:1, 10:1 and 6:1 were used, respectively. These batches were thoroughly mixed and degassed prior to use for device fabrication. The control layer mold was spin coated with a thick layer (~1 mm) of 6:1 PDMS and baked at 80° C. for 7 mins. A thin layer of 15:1 PDMS was spin coated on the fluidic layer mold. The device was designed such that the valve regions on the device were placed in areas surrounded by shallow fluidic channels, ensuring uniform coverage of these regions with a thin layer of PDMS. The PDMS on the fluidic layer mold was then baked at 80° C. for 6 minutes. The PDMS was removed from the control layer mold and the control layer was cut to the exact size of the valve regions on the device, while not covering any channels higher than 50 µm on the device (FIG. 9). The control layer PDMS pieces were aligned with baked PDMS layer on the fluidic layer mold under a stereoscope. The fluidic layer mold with the aligned control layer was baked at 80° C. for 20 mins to promote adhesion between the control layer and the fluidic layer. Following this, 49.5 g of 10:1 PDMS was poured on the fluidic layer mold, covering all features on the fluidic layer mold with a 3-4 mm thick layer of PDMS. The fluidic layer mold was then baked for at least 30 minutes at 80° C. Following this, the PDMS was removed from the fluidic layer mold and individual devices were cut. Fluidic access holes were then punched into the device and the device was bonded to a coverglass through oxygen plasma treatment.

Fusion Zone Design

Figure 10:
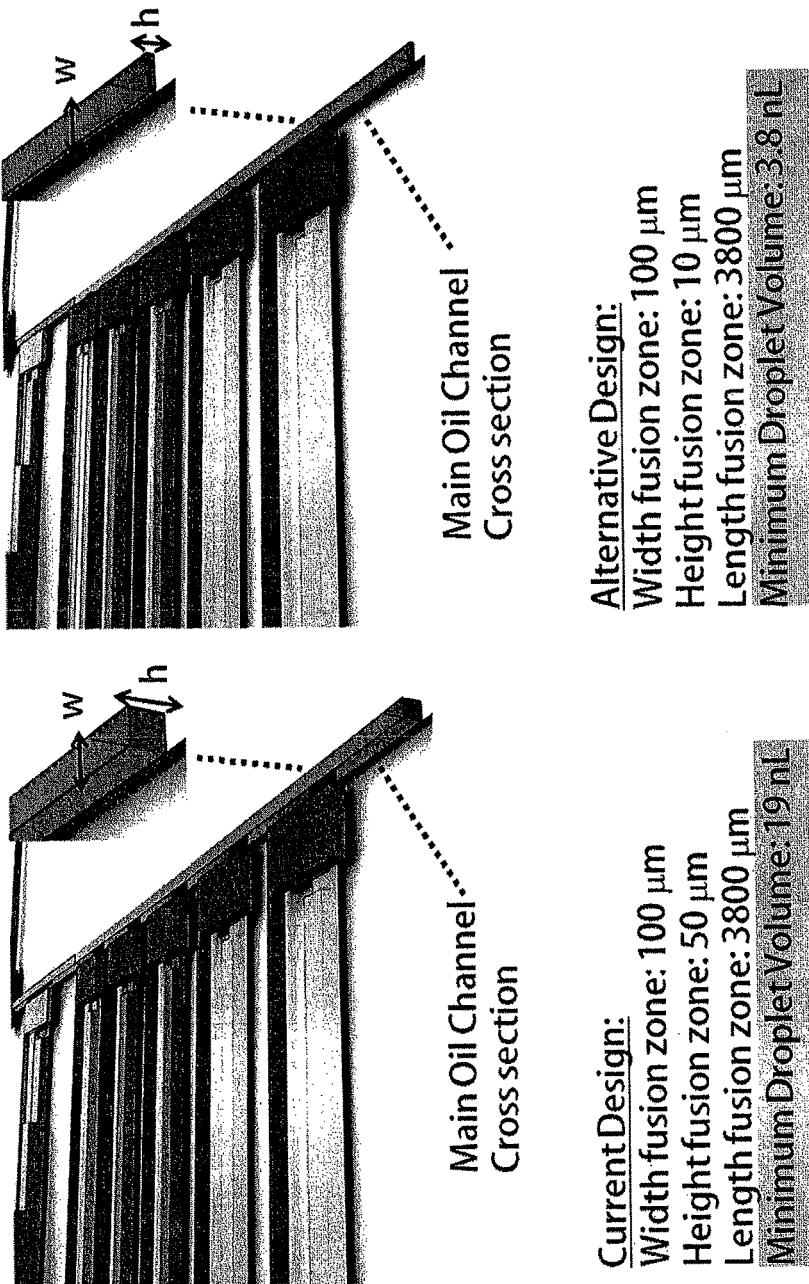
FIG. 10 shows a fusion zone design for robust reagent injection in sample droplets with different volumes according to an embodiment of the current invention.

An important aspect of an embodiment of our microfluidic device is the robust synchronization-free fusion mechanism. This mechanism utilizes the cross-sectional area of the central channel on the microfluidic device for the merging operation. FIG. 10 demonstrates the design criteria of the fusion region of an embodiment of our device. In the current example, the dimensions of the fusion zone, defined as the distance between the first and last reagent inlet (3800 µm), height (50 µm) and width (100 µm) of the central channel determine the volume of the fusion zone (19 nL). This volume of the fusion zone corresponds to the minimum volume of the sample daughter droplet, such that the droplet spans the entire length of all the reagent injection sites on the chip. As a result, the sample daughter droplet position doesn't need to be finely controlled to inject different reagents in it. If there is a need for smaller reaction volumes, the cross-sectional area of the central channel can be modified to reduce the minimum volume of the sample daughter droplet required. For instance, reducing the fusion zone channel height from 50 µm to 10 µm will results in reduction in minimum required droplet volume from 19 nL to 3.8 nL (FIG. 10). A similar approach can be used to accommodate more than four reagent inlets on the chip.

Serial Sample Loading System

Figure 11A:
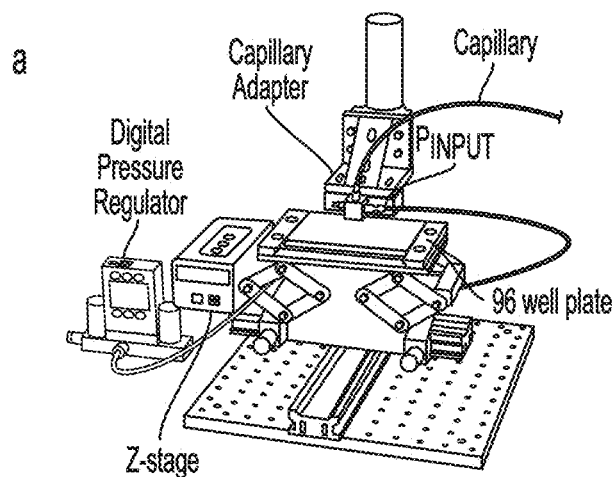
FIGS. 11A and 11B shows an example of a custom Serial Sample Loading (SSL) System according to an embodiment of the current invention.
Figure 11B:
Figure 11B:
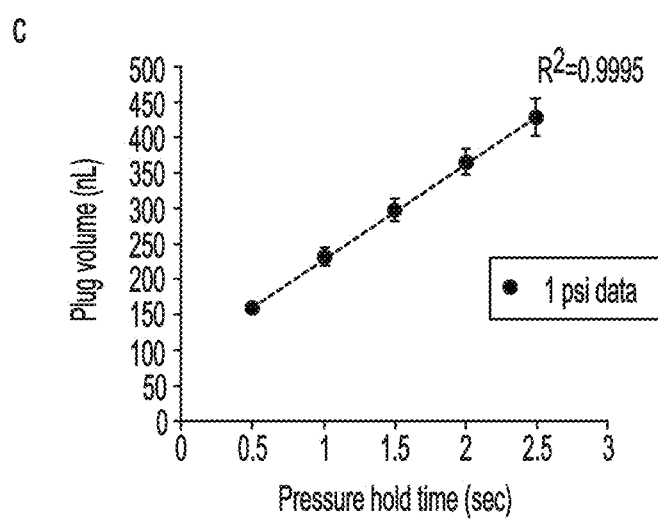

FIG. 11 shows an actual assembled Serial Sample Loading (SSL) system for sample library generation according to an embodiment of the current invention. The SSL system consists of 1) a custom-made capillary adapter, 2) an automated Z-stage, 3) manual X- and Y-stages 4) a multi-well plate and 5) an Electronic Pressure Controller. The capillary adapter was designed in Solidworks (Solidworks Corp.) and then fabricated by the staff at the Physical Sciences Machine Shop at Johns Hopkins University. A motorized Lab Jack (L490MZ/M, Thorlabs) was used as the automated Z-stage. The manual X and Y stages were purchased from Melles Griot (Albuquerque, N. Mex.). In its current form, the SSL system was designed to be compatible with the Costar 96-well plates (Corning). The Electronic Pressure Controller (PCD-100PSIG-D-PCV03, Alicat Scientific) used in the SSL system is a dual valve pressure controller designed for pressure control in a closed volume. All other structural components of the SSL system were purchased from Thorlabs (Newton, N.J.). Custom software developed in LabVIEW was used to control the Z-motion of the automated Z-stage and the injection pressure applied by the Electronic Pressure Controller.

The capillary adapter in the SSL system features three different ports, which are designed for accepting a microcapillary input, a pressure input and an output for gauging pressure inside a sealed sample well. We attached NanoPorts (Idex Health and Science) at these three ports for consistent leak free connections with tubing corresponding to each port. The bottom surface of the capillary adapter also holds a silicone sealing ring, fabricated from Silicone Septa (1395-32SS, Corning) used to seal a sample well with the capillary adapter. All the three ports on the capillary adapter are routed to the bottom surface of the capillary adapter where they open into a sealed sample well. For most of our experiments, a silica microcapillary (360 µm OD and 200 µm ID) was attached to the capillary input of the capillary adapter, unless specified otherwise. The pressure input was connected to the output of the pressure controller. The pressure gauge port was unused and kept plugged for all the experiments. Prior to use, the silica microcapillary is treated with Aquapel™ (PPG Industries).

CONCLUSION

In the above examples, we have demonstrated a platform capable of preparing droplets from combinational mixtures of a large number of samples and reagents. This is accomplished by synchronization-free and detection-free fusion of sample daughter droplets and reagents. A benefit of this architecture can include the ability to scale this device to analyze N samples against M reagents (N×M) where N can range from hundreds to thousands without accompanying increase in device complexity. Additional reagent set multiplexing can be accomplished analogously by introducing linear arrays of reagent set plugs similar to sample introduction. Furthermore, this design allows for spatial indexing, by maintaining the sequence of droplets from generation throughout incubation, precluding the need for barcoding.

Some components can include: a unique SSL system which uses pressure to inject uniform volumes of sample into a capillary directly from an industry standard multi-well plate. This capillary is then interfaced with a microfluidic device using a novel capillary-to-chip connection. The microfluidic device is capable of combinatorial screening operations. Robust synchronization-free reagent injection is performed on the device based on a design which capitalizes on droplet elongation in the fusion zone on the device. In an embodiment, up to 4 reagent droplets can be fused with a single sample droplet. However, by employing the same concept many more reagent inlets can be introduced on chip to perform merging operations. In addition, we have demonstrated a technique for reagent injection in droplets that capitalizes on controlling droplet surface chemistry by controlling surfactant concentration at different regions on the chip. That is, we have demonstrated a surfactant-free environment in the fusion zone on the device, thereby promoting reagent injection in sample droplets while the droplets are stabilized by surfactant in the incubation region.

For the microfluidic chip design, several areas can be explored to further enhance the operation of the chip. To make the transition of sample plugs from a capillary to the microfluidic device more gradual a photolithography process employing a grayscale mask could be used. This approach can generate very gradual reduction in channel cross section from a large capillary to shallow microfluidic channels on the device compared to the step reduction demonstrated in the example above. Furthermore, reagents may be loaded in cartridge format to further enhance multiplexing capabilities. We expect the platform described here to be a promising candidate for combinatorial screening applications using droplet microfluidics.

REFERENCES

1. S. Y. Teh, R. Lin, L. H. Hung and A. P. Lee, Lab. Chip, 2008, 8, 198-220 (DOI:10.1039/b715524g).
2. A. Huebner, S. Sharma, M. Srisa-Art, F. Hollfelder, J. B. Edel and A. J. Demello, Lab. Chip, 2008, 8, 1244-1254 (DOI:10.1039/b806405a).
3. R. R. Pompano, W. Liu, W. Du and R. F. Ismagilov, Annu. Rev. Anal. Chem. (Palo Alto Calif.), 2011, 4, 59-81 (DOI:10.1146/annurev.anchem.012809.102303).
4. M. T. Guo, A. Rotem, J. A. Heyman and D. A. Weitz, Lab. Chip, 2012, (DOI:10.1039/c2lc21147e).
5. H. Song, D. L. Chen and R. F. Ismagilov, Angew. Chem. Int. Ed Engl., 2006, 45, 7336-7356 (DOI:10.1002/anie.200601554).
6. P. Kumaresan, C. J. Yang, S. A. Cronier, R. G. Blazej and R. A. Mathies, Anal. Chem., 2008, 80, 3522-3529 (DOI:10.1021/ac800327d).
7. N. R. Beer, B. J. Hindson, E. K. Wheeler, S. B. Hall, K. A. Rose, I. M. Kennedy and B. W. Colston, Anal. Chem., 2007, 79, 8471-8475 (DOI:10.1021/ac701809w).
8. M. M. Kiss, L. Ortoleva-Donnelly, N. R. Beer, J. Warner, C. G. Bailey, B. W. Colston, J. M. Rothberg, D. R. Link and J. H. Leamon, Anal. Chem., 2008, 80, 8975-8981.
9. A. Huebner, M. Srisa-Art, D. Holt, C. Abell, F. Hollfelder, A. J. deMello and J. B. Edel, Chem. Commun. (Camb), 2007, (12), 1218-1220 (DOI:10.1039/b618570c).
10. J. Clausell-Tormos, D. Lieber, J. C. Baret, A. El-Harrak, O. J. Miller, L. Frenz, J. Blouwolff, K. J. Humphry, S. Koster, H. Duan, C. Holtze, D. A. Weitz, A. D. Griffiths and C. A. Merten, Chem. Biol., 2008, 15, 427-437 (DOI:10.1016/j.chembiol.2008.04.004).
11. J. C. Baret, O. J. Miller, V. Taly, M. Ryckelynck, A. El-Harrak, L. Frenz, C. Rick, M. L. Samuels, J. B. Hutchison, J. J. Agresti, D. R. Link, D. A. Weitz and A. D. Griffiths, Lab. Chip, 2009, 9, 1850-1858 (DOI:10.1039/b902504a).
12. W. Shi, J. Qin, N. Ye and B. Lin, Lab. Chip, 2008, 8, 1432-1435 (DOI:10.1039/b808753a).
13. W. Shi, H. Wen, Y. Lu, Y. Shi, B. Lin and J. Qin, Lab. Chip, 2010, 10, 2855-2863 (DOI:10.1039/c0lc00256a).
14. B. Sobrino, M. Brion and A. Carracedo, Forensic Sci. Int., 2005, 154, 181-194 (DOI:10.1016/j.forsciint.2004.10.020).
15. P. K. Gupta, S. Rustgi and R. R. Mir, Heredity (Edinb), 2008, 101, 5-18 (DOI:10.1038/hdy.2008.35).
16. J. Ragoussis, Annu. Rev. Genomics Hum. Genet., 2009, 10, 117-133 (DOI:10.1146/annurev-genom-082908-150116).
17. B. Veldhuisen, C. E. van der Schoot and M. de Haas, Vox Sang., 2009, 97, 198-206 (DOI:10.1111/j.1423-0410.2009.01209.x).
18. R. Tewhey, J. B. Warner, M. Nakano, B. Libby, M. Medkova, P. H. David, S. K. Kotsopoulos, M. L. Samuels, J. B. Hutchison, J. W. Larson, E. J. Topol, M. P. Weiner, O. Harismendy, J. Olson, D. R. Link and K. A. Frazer, Nat. Biotechnol., 2009, 27, 1025-1031 (DOI:10.1038/nbt.1583).
19. E. Brouzes, M. Medkova, N. Savenelli, D. Marran, M. Twardowski, J. B. Hutchison, J. M. Rothberg, D. R. Link, N. Perrimon and M. L. Samuels, Proc. Natl. Acad. Sci. U.S.A., 2009, 106, 14195-14200 (DOI:10.1073/pnas.0903542106).
20. A. B. Theberge, E. Mayot, A. El Harrak, F. Kleinschmidt, W. T. Huck and A. D. Griffiths, Lab. Chip, 2012, 12, 1320-1326 (DOI:10.1039/c2lc21019c).
21. A. R. Abate, T. Hung, P. Mary, J. J. Agresti and D. A. Weitz, Proc. Natl. Acad. Sci. U.S.A., 2010, 107, 19163-19166 (DOI:10.1073/pnas.1006888107).

22. L. Li, D. Mustafi, Q. Fu, V. Tereshko, D. L. Chen, J. D. Tice and R. F. Ismagilov, *Proc. Natl. Acad. Sci. U.S.A.*, 2006, 103, 19243-19248 (DOI:10.1073/pnas.0607502103).
23. J. Q. Boedicker, L. Li, T. R. Kline and R. F. Ismagilov, *Lab. Chip*, 2008, 8, 1265-1272 (DOI:10.1039/b804911d).
24. S. Zeng, B. Li, X. Su, J. Qin and B. Lin, *Lab. Chip*, 2009, 9, 1340-1343 (DOI:10.1039/b821803j).
25. F. Guo, K. Liu, X. Ji, H. Ding, M. Zhang, Q. Zeng, W. Liu, S. Guo and X. Zhao, *Appl. Phys. Lett.*, 2010, 97, 233701-3.
26. H. Wang, K. Liu, K. J. Chen, Y. Lu, S. Wang, W. Y. Lin, F. Guo, K. Kamei, Y. C. Chen, M. Ohashi, M. Wang, M. A. Garcia, X. Z. Zhao, C. K. Shen and H. R. Tseng, *ACS Nano*, 2010, 4, 6235-6243 (DOI:10.1021/nn101908e).
27. M. A. Unger, H. P. Chou, T. Thorsen, A. Scherer and S. R. Quake, *Science*, 2000, 288, 113-116.
28. C. M. Puleo and T. H. Wang, *Lab. Chip*, 2009, 9, 1065-1072 (DOI:10.1039/b819605b).
29. C. M. Puleo, H. C. Yeh, K. J. Liu and T. H. Wang, *Lab. Chip*, 2008, 8, 822-825 (DOI:10.1039/b717941c).
30. T. D. Rane, C. M. Puleo, K. J. Liu, Y. Zhang, A. P. Lee and T. H. Wang, *Lab. Chip*, 2010, 10, 161-164 (DOI:10.1039/b917503b).
31. J. Melin and S. R. Quake, *Annu. Rev. Biophys. Biomol. Struct.*, 2007, 36, 213-231 (DOI:10.1146/annurev.biophys.36.040306.132646).
32. M. D. Abramoff, P. J. Magalhaes and S. J. Ram, *Biophotonics International*, 2004, 11, 36-42.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of screening a plurality of samples, comprising:
    obtaining a sequential stream of sample plugs, the sample plugs being completely separated from each other by a carrier fluid, the sequential stream of sample plugs comprising a first sample plug from a first sample substance and a second sample plug from a second sample substance, the first sample substance being different from the second sample substance;
    generating a sequential stream of droplets from said sequential stream of sample plugs using a selectively controllable microfluidic system, wherein each sample plug, in sequence, is divided into a plurality of droplets to form the sequential stream of droplets such that the first sample plug is divided into a first plurality of droplets and the second sample plug is divided into a second plurality of droplets;
    selectively adding a first reagent from a plurality of reagents to a selected first droplet of said sequential stream of droplets and adding a second reagent from the plurality of reagents to a selected second droplet of said sequential stream of droplets in sequential order using said selectively controllable microfluidic system when the selected first droplet and the selected second droplet are, respectively, within a reagent adding section of the selectively controllable microfluidic system to provide a stream of treated first and second droplets in said sequential order corresponding to said sequential stream of droplets, wherein the second reagent is different from the first reagent;
    measuring at least one property of the first treated droplet and the second treated droplet in said sequential order; and
    identifying measured droplets based on said sequential order during said measuring using information concerning an identity of said plug from which the selected first droplet or the selected second droplet, or both of said sequential stream of droplets is generated and an identity of said first reagent added to the selected first droplet and an identity of said second reagent added to the selected second droplet.

2. A method of screening a plurality of samples according to claim 1, further comprising adding a stabilizer to each selected droplet of said sequential stream of droplets after said adding at least one reagent to help prevent adjacent droplets from coalescing.

3. A method of screening a plurality of samples according to claim 1, further comprising regulating a temperature of an incubation section of said selectively controllable microfluidic system after said adding at least one reagent and prior to said measuring.

4. A method of screening a plurality of samples according to claim 1, wherein said obtaining the sequential stream of sample plugs comprises obtaining at least one capillary tube that is loaded with the sequential stream of sample plugs with the carrier fluid between adjacent sample plugs.

5. A method of screening a plurality of samples according to claim 4, wherein said obtaining the sequential stream of sample plugs comprises loading said at least one capillary from a multi well plate.

6. A method of screening a plurality of samples according to claim 4, wherein said loaded using an automated loading system.

7. A method of screening a plurality of samples according to claim 1, wherein said obtaining the sequential stream of sample plugs comprises loading a capillary with the sequential stream of sample plugs.

8. A method of screening a plurality of samples according to claim 7, wherein loading the capillary with the sequential stream of sample plugs comprises:
    moving the sequential stream of sample plugs through the capillary into one or more channels of a microfluidic device, and
    generating the sequential stream of droplets in the microfluidic device.

9. A method of screening a plurality of samples according to claim 8, wherein moving the sequential stream of sample plugs through the capillary into the one or more channels of the microfluidic device comprises moving the sequential stream of sample plugs through a plurality of sequentially connected capillary sections of decreasing size from a larger size of an initial capillary section to a smaller size of the one or more channels.

* * * * *

UNITED STATES PATENT AND TRADEMARK OFFICE
CERTIFICATE OF CORRECTION

PATENT NO. : 10,222,392 B2
APPLICATION NO. : 15/146319
DATED : March 5, 2019
INVENTOR(S) : Wang et al.

Page 1 of 1

It is certified that error appears in the above-identified patent and that said Letters Patent is hereby corrected as shown below:

In the Specification

Column 1, after Line 18 and before the heading "BACKGROUND" please insert the following:
--STATEMENT OF GOVERNMENT INTEREST
This invention was made with government support under grant number CA120742 awarded by the National Institutes of Health. The government has certain rights in the invention.--

Signed and Sealed this
Twenty-ninth Day of September, 2020

Andrei Iancu
*Director of the United States Patent and Trademark Office*